US011896760B2

(12) United States Patent
Johansen et al.

(10) Patent No.: US 11,896,760 B2
(45) Date of Patent: *Feb. 13, 2024

(54) BREATHING DEVICE, APP AND INTERACTION THEREBETWEEN

(71) Applicant: Rehaler APS, Ålsgårde (DK)

(72) Inventors: Troels Johansen, Aarhus C (DK); Erik Othel-Jacobsen, Hellebæk (DK); Asger Johansen, København S (DK)

(73) Assignee: Rehaler APS, Ålsgårde (DK)

( * ) Notice: Subject to any disclaimer, the term of this patent is extended or adjusted under 35 U.S.C. 154(b) by 664 days.

This patent is subject to a terminal disclaimer.

(21) Appl. No.: 16/637,915

(22) PCT Filed: Aug. 23, 2018

(86) PCT No.: PCT/DK2018/050206
§ 371 (c)(1),
(2) Date: Feb. 10, 2020

(87) PCT Pub. No.: WO2019/037827
PCT Pub. Date: Feb. 28, 2019

(65) Prior Publication Data
US 2020/0179627 A1 Jun. 11, 2020

(30) Foreign Application Priority Data

Aug. 23, 2017 (DK) .......................... PA 2017 70635
Jul. 24, 2018 (DK) .......................... PA 2018 70502

(51) Int. Cl.
A61M 16/00 (2006.01)

(52) U.S. Cl.
CPC .... *A61M 16/0045* (2013.01); *A61M 16/0078* (2013.01); *A61M 2202/0225* (2013.01); *A61M 2230/205* (2013.01)

(58) Field of Classification Search
CPC .. A61M 16/0078; A61M 16/81; A61M 16/84; A61M 16/0045; A61M 2202/0225; A61M 16/0051; A63B 23/18
See application file for complete search history.

(56) References Cited

U.S. PATENT DOCUMENTS 3,949,984 A * 4/1976 Navara ................. A63B 23/18
482/13
4,192,301 A * 3/1980 Hardwick ......... A61M 16/0045
128/205.24

(Continued)

FOREIGN PATENT DOCUMENTS

DE  19912337 C1  8/2000
EP  1629859 A1   3/2006

(Continued)

OTHER PUBLICATIONS

English Translation of DE19912337C1, http://espacenet.com, 2022 (Year: 2022).*

(Continued)

*Primary Examiner* — Kathryn E Ditmer
(74) *Attorney, Agent, or Firm* — Knobbe Martens Olson & Bear LLP

(57) ABSTRACT

The invention relates to a breathing device (1), comprising a mouthpiece (2) forming a breathing channel to form a connection between a first (3) end and a second (4) end of the mouthpiece (2). The first (3) end is configured for a user breathing into the mouthpiece through a breathing opening (5). An at least partly flexible rebreathing air chamber (6) is arranged in fluid communication with the second (4) end of the mouthpiece, thereby being in fluid connection with the breathing channel through the second end of the mouthpiece (2). The rebreathing air chamber is formed by at least partly flexible wall section(s). A wall member (7) is arranged at the second (4) end of the mouthpiece and/or attached to the (Continued)

rebreathing air chamber (6). The wall member (7) comprises one or more through-going openings (8) provided in the wall member (7) and/or in the breathing channel, allowing fluid communication between the rebreathing air chamber (6) and the surrounding atmosphere.

11 Claims, 19 Drawing Sheets

(56) References Cited

U.S. PATENT DOCUMENTS

| | | | | |
|---|---|---|---|---|
| 4,221,381 | A | * | 9/1980 | Ericson .................. A63B 23/18 73/239 |
| 4,275,722 | A | * | 6/1981 | Sorensen .......... A61M 16/0045 128/914 |
| 4,301,810 | A | * | 11/1981 | Belman .................. A61B 5/097 482/13 |
| 4,628,926 | A | * | 12/1986 | Duncan ............. A61M 16/0045 128/914 |
| 4,919,132 | A | | 4/1990 | Miser |
| 5,647,345 | A | * | 7/1997 | Saul .................. A61M 16/0045 128/200.24 |
| 9,643,048 | B1 | * | 5/2017 | Danford ........... A63B 21/00069 |
| 2002/0035927 | A1 | * | 3/2002 | Kutt ....................... B01D 53/62 96/111 |
| 2006/0130839 | A1 | * | 6/2006 | Bassovitch ....... A61M 16/0045 128/914 |
| 2008/0314386 | A1 | * | 12/2008 | Myklebust ........ A61M 16/0084 128/205.15 |
| 2008/0319277 | A1 | | 12/2008 | Bradley |
| 2009/0239711 | A1 | * | 9/2009 | Foley .................... A63B 23/18 482/13 |
| 2012/0240935 | A1 | * | 9/2012 | Johansen ............... A61M 16/06 128/205.17 |
| 2012/0270703 | A1 | | 10/2012 | Foley et al. |
| 2017/0157461 | A1 | * | 6/2017 | Lyapko ................. A63B 23/18 |

FOREIGN PATENT DOCUMENTS

| | | |
|---|---|---|
| JP | 11-500633 A | 1/1999 |
| JP | 2010-501255 A | 1/2010 |
| JP | 2015-514511 A | 5/2015 |
| WO | WO-2016098099 A1 * 6/2016 | ........ A61M 16/0048 |
| WO | WO 2017/140322 A1 | 8/2017 |

OTHER PUBLICATIONS

Office Action for JP 2020-511515 dated May 10, 2022.
Office Action for CN 201880054654.9 dated Feb. 25, 2022.
International Search Report for PCT/DK2018/050206 dated Dec. 11, 2018.

* cited by examiner

BREATHING DEVICE, APP AND INTERACTION THEREBETWEEN

CROSS REFERENCE TO RELATED APPLICATIONS

This application is a U.S. National Phase Application of PCT International Application Number PCT/DK2018/050206, filed on Aug. 23, 2018, designating the United States of America and published in the English language, which is an International Application of and claims the benefit of priority to Danish Patent Application No. PA 2017 70635, filed on Aug. 23, 2017, and Danish Patent Application No. PA 2018 70502, filed on Jul. 24, 2018. The disclosures of the above-referenced applications are hereby expressly incorporated by reference in their entireties.

FIELD OF THE INVENTION

The present invention relates to a breathing device for increasing and/or balancing and/or maintaining a specific level of $CO_2$ in the inhaled air. Several breathing devices for increasing the level of $CO_2$ in inhaled air are known. Such devices may be a simple mask covering the user's mouth and nose or a mask connected to a bag, which is able to expand and retract during breathing. The mask may be equipped with a valve or similar which allows fresh air into the mask.

BACKGROUND OF THE INVENTION

In a range of different common medical disorders (among them migraine, epilepsy, post-spinal headache, febrile seizures, idiopathic dyspnoea, the hyperventilation syndrome, panic anxiety, asthma, and certain heart conditions) it has been demonstrated that a positive treatment effect can be obtained by raising the $CO_2$ concentration in the patient's inspired air. In the body, raising the $CO_2$ concentration will, among other effects, lower the pH value of the bodily fluids, increase the cerebral blood flow and lower the excitability of the nervous system.

OBJECT OF THE INVENTION

An object of the present invention is to provide an improvement of breathing devices for increasing and/or maintaining specific levels of $CO_2$ in the inhaled air.

Another object of the present invention is to provide a device which may relieve the symptoms of migraine, post-spinal headache or other types of headache, or optionally inhibit and/or prevent an attack of migraine in a user suffering from migraine.

A further object is to provide a device which may be used for relieving or preventing epileptic attacks and/or febrile seizures.

A further object is to provide a device which may be used for the preventive treatment of asthma.

A further object is to provide a device which may be used for improving rehabilitation after cardiac arrest.

A further object is to provide a device which may serve to increase the cerebral blood flow and oxygen delivery to the brain by the vasodilatory action of $CO_2$.

A further object is to provide a device which during use may decrease the excitability of the nervous system by inducing acidosis in a user, mediated by increasing the inspired partial pressure of $CO_2$.

A further object is to provide a device which may serve to signalize to the user a new setting for the breathing device for optimization of the Rebreathing Ratio (RBR).

SUMMARY OF THE INVENTION

The invention relates, in a first aspect, to a breathing device, comprising
- a mouthpiece forming a breathing channel to form a connection between a first end and a second end of the mouthpiece, the first end may be configured for a user breathing into the mouthpiece through a breathing opening
- an at least partly flexible rebreathing air chamber arranged in fluid communication with the second end of the mouthpiece, thereby being in fluid connection with the breathing channel through the second end of the mouthpiece, the rebreathing air chamber may be formed by at least partly flexible wall section(s)
- a wall member preferably arranged at the second end of the mouthpiece and/or attached to the rebreathing air chamber, the wall member may comprise one or more through-going openings provided in the wall member and/or in the breathing channel, allowing fluid communication between the rebreathing air chamber and the surrounding atmosphere.

The through-going openings may have a first conductance $G_{out}$, where $G_{out}$ may be defined as the total volume flow per second through the openings divided by the pressure difference between the inside the rebreathing air chamber and the surrounding atmosphere. The rebreathing air chamber may be impermeable to gas and have a second conductance $G_{expand}$, where $G_{expand}$ may be defined as the volume expansion per second of the rebreathing chamber divided by the pressure difference between the inside the rebreathing air chamber and the surrounding atmosphere. The through-going openings and the rebreathing air chamber may be configured to provide a RBR defined as $RBR = G_{expand}/(G_{out}+G_{expand})$ between 0.5 and 0.95, or may be between 0.2 and 0.65. RBR may in this context be measured by means of an experimental setup described herein.

Preferably, one or more of the through-going openings are re-closable and/or adjustable in size.

Preferably, the one or more of said through-going openings may be non-closable.

The breathing device may further comprise a slider configured for covering a portion of the through-going openings provided on the wall member. The slider is preferably arranged between two parallel longitudinal wall sections e.g. between two longitudinal edges of the wall member, in such a way that the slider provides an opening into the rebreathing air chamber when moved. The slider is preferably configured for adjusting the flow of air into and/or out of the rebreathing air chamber, as well as for adjusting the RBR value.

The through-going openings may be in the form of longitudinal vent holes extending horizontally between the wall sections.

The longitudinal vent holes may extend vertically between the wall sections.

The longitudinal vent holes may be obliquely shaped, the vent holes preferably proceeding through the wall member in an oblique manner relative to the orientation of the plane defined by the wall member.

Preferably, the vent holes proceed through the wall in an angle of 10-80 degrees, such as 20-70 degrees, preferably 60 degrees (all angles are given relative to the plane defined by the wall member). The vent holes may be configured for providing a guided directional outflow outside the breathing device away from the user's face.

Preferably, the size of the slider may be selected so it can not cover all through-going openings and/or vent holes.

The longitudinal vent holes may have an increasing length in order to provide approximately equal flow resistance change increments when the slider is moved incrementally from the first to the second position or vice-versa, or to provide a stepwise and linear pressure drop increments when said slider (9) is moved from a first position to a second position.

The wall member is preferably pivotally connected to the mouth piece and the connection comprises a latch, which may be configured for adjusting an angle between the wall member and the mouthpiece.

Preferably, the latch may comprise
  a hinged and generally flat member rotatably connected to the mouth piece by a hinge,
  a protruding member rigidly arranged on the wall member, said protruding member being anvil-like shaped with arms,
wherein:
  the flat member may comprise an opening through which the protruding member extends with the arms extending above an upper surface of the flat member,
  the opening may comprise two landings, a tapering section and two uprights, where the tapering section may be arranged in-between the two uprights and the two landings.

The breathing device may further comprise a SpO2-sensor, configured for measuring the oxygen level of the user's blood, and/or a side-inlet arranged in the mouth piece. The side-inlet may be arranged so as to extract a portion of the air flowing through the breathing channel, preferably for forwarding the extracted air to a $CO_2$ determining device, so as to determine the $CO_2$ level of the user's exhaled breath.

Preferably, the breathing device may arranged inside a packaging, such as a sealed packaging.

Preferably, the breathing device may arranged inside the packaging in a folded configuration.

Preferably, the breathing device may comprises a teeth-support comprising a ridge arranged at the first end and preferably encircling the breathing opening, and preferably further comprising a traversing projection that may be arranged distant from the ridge preferably on a lower surface of the mouth piece.

In second aspect, the invention relates to a nose clamp preferably comprising
  a bendable elongated strip, such as a strip made from aluminium or titanium, and
  a coating surrounding the strip preferably on all sides, such as a coating made from silicone, rubber, leather and/or thermoplastic elastomer (TPE).

Preferably, the nose clamp may have an elastic limit between 1 and 10 newton, such as between 2 and 8 newton.

In a third aspect, the invention may relate to a kit of parts, preferably for increasing and/or balancing and/or maintaining a specific level of $CO_2$ in the inhaled air, comprising a breathing device, preferably being a breathing device according to any of the embodiments of the present invention and a SpO2-sensor, such as a stand-alone SpO2 sensor and/or a $CO_2$ sensor fluidly connected to the breathing device. Such a breathing device may preferably be a device as disclosed herein or a breathing device in general being configured for providing a rebreathing ratio, such as being configured for adjusting the rebreathing ratio.

Preferably, the kit of parts may comprising one or a plurality of breathing devices according to the first aspect of the invention, preferably each arranged inside a packaging, and one or more single sensors, such as SpO2 sensors, wherein the plurality may be 2, 3, 4, 5, 6, 7, 8, 9, 10, 11, 12 or even more.

Preferably, the kit of part may further comprise a nose clamp according to the second aspect of the invention.

In a fourth aspect, the invention may relate to a method for adjusting the RBR. The method may utilize a breathing device with an adjustable RBR and a computer preferably configured to automatically determine whether to change the RBR based on a user's response to a questionnaire and/or based on measurements of CO2 and/or SpO2 levels. The RBR may in some embodiments be changed via a setting of a slider's position in embodiments comprising such a slider, each setting corresponding to a specific position of the slider on the wall element to cover a portion of the longitudinal vent holes. In other embodiments, the RBR being preferably changed by closing, opening or changing the size of a number of the through-going openings (8), which closing may include some or all of vent holes if such are present. The method may comprise the following steps:
  providing measurement(s) of a user's blood oxygen level and/or end tidal CO2 by use of the SpO2-sensor and/or a $CO_2$ sensor,
  executing a questionnaire containing questions relating the user's response to the use of the breathing device during use of the breathing device, in response thereto determining by use of the computer whether to change the RBR, and
  if the RBR is determined to be changed, signalling to the user a new setting for the breathing device.

A method for adjusting the RBR may be applied to the kit of parts.

The computer may be a smartphone.

The computer such as a portable device may be a tablet or a smartphone. The method may be implemented as an App.

Preferably, the computer has a number of pre-stored baseline settings, each setting corresponds to a slider position or a number of said through-going openings being closed.

Preferably, the computer has a number of pre-stored baseline settings, each setting corresponds to a geographical position.

Preferably, the computer has a number of pre-stored baseline settings, each setting corresponds to an iHealth information and/or previous changes in the RBR and/or user data such as gender, age and type of disease.

The individual aspects of the present invention may each be combined with any of the other aspects. These and other aspects of the invention will be apparent from the following description with reference to the described embodiments.

In the present context, a number of terms are used in a manner being ordinary to a skilled person; however, some of these terms are elucidated below:

Rebreathing air chamber is preferably used to mean/denote the bag of the breathing device.

RBR is preferably used to mean/denote the Rebreathing Ratio, which is the ratio A/B where A is the subset of the inspired air flow consisting of gas which has previously been breathed out and B is the total inspired air flow.

Slider is preferably used to mean/denote a wall element, configured for providing an opening into the breathing device. The slider may have other shapes, such as a rotary valve.

By partly flexible is preferably meant that at least a part of the wall(s) forming the rebreathing air chamber is flexible whereas another part is non-flexible.

$G_{out}$ is preferably used to mean/denote the conductance of the through-going openings, i.e. the volume flow through the through-going openings per second per pressure difference across the through-going openings.

$G_{expand}$ is preferably used to mean/denote the volume expansion per second of the rebreathing chamber divided by the pressure difference between the inside of the rebreathing air chamber and the surrounding atmosphere, or alternatively the inverse of the chamber's resistance to expansion.

Setting is preferably used to mean/denote an adjustment of the breathing device's RBR e.g. by moving the slider to a specific position on the wall member, or by closing, opening or changing the size of a number of the through-going openings.

First position is preferably used to mean/denote a fully closed position of the slider, enabling a minimum fluid communication between the rebreathing air chamber and the surrounding atmosphere.

Second position is preferably used to mean/denote a fully open position of the slider, enabling a maximum fluid communication between the rebreathing air chamber and the surrounding atmosphere.

Execute is preferably used to mean/denote that a series of questions are asked to the user and a response from the user is given.

BRIEF DESCRIPTION OF THE FIGURES

The figures show one way of implementing the present invention and are not to be construed as being limiting to other possible embodiments falling within the scope of the attached claim set.

FIG. 12 illustrates a side-view of the nose clamp 17 in a straight and a curved configuration, whereas FIG. 13 illustrates a three-dimensional view of the nose clamp in the straight and the curved configuration. FIG. 14 illustrates elements of the nose claims including cross sectional views FIG. 15 schematically illustrates an experimental setup for measuring the elastic limit of a nose clamp;

DETAILED DESCRIPTION OF AN EMBODIMENT

Figure 1:
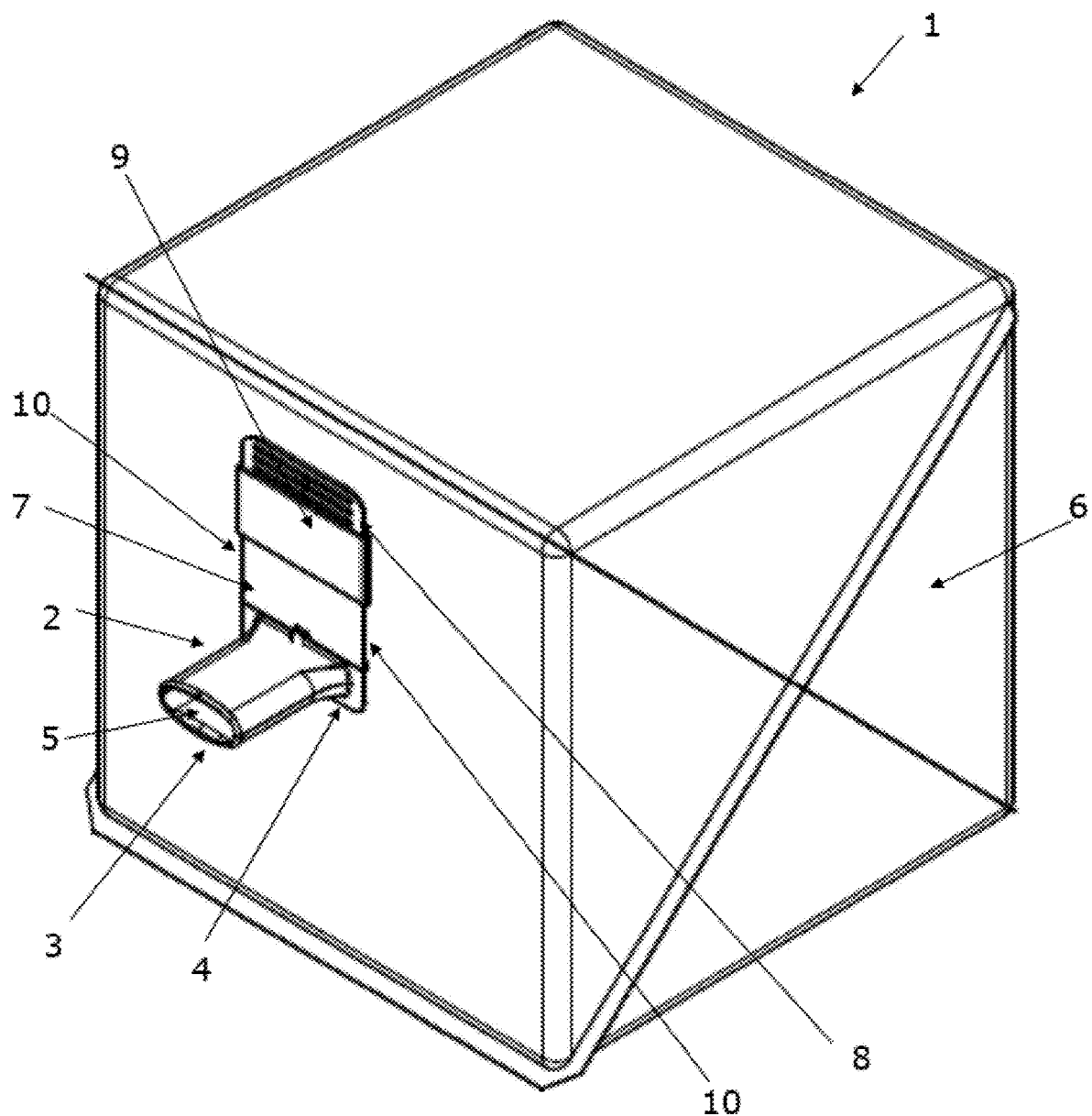
FIG. 1 illustrates a breathing device composed of a rebreathing air chamber and a mouthpiece.

Reference is made to FIG. 1, illustrating a breathing device 1. The breathing device 1, comprises a mouthpiece 2 forming a breathing channel to form a connection between a first 3 end and a second 4 end of the mouthpiece 2. The first end 3 is configured for a user breathing into the mouthpiece through a breathing opening 5. An at least partly flexible rebreathing air chamber 6 is arranged in fluid communication with the second 4 end of the mouthpiece, thereby being in fluid connection with the breathing channel through the second end 4 of the mouthpiece 2. The rebreathing air chamber 6 is formed by at least partly flexible wall section(s).

A wall member 7 is arranged at the second end 4 of the mouthpiece and attached to the rebreathing air chamber 6. The wall member 7 comprises through-going openings 8 provided in the wall member 7 allowing fluid communication between the rebreathing air chamber 6 and the surrounding atmosphere. The mouthpiece is adapted to engage with a user's mouth, so the user can breathe into the breathing channel. However, the mouthpiece can also be used as an intermedia between a user's mouth and an additional connector, such as a facial mask, which is connected to the mouthpiece 2.

The rebreathing air chamber may be detachably attached to the second end 4 of the mouthpiece 2. The rebreathing air chamber 6 has a volume between 0.5 liter and 16 liters, such as 2 liters and 8 liters, preferably between 3 liters and 6 liters. The breathing channel has a cross-section of at least 1.0 $cm^2$, such at least 1.5 $cm^2$, preferably at least 2.0 $cm^2$. The wall sections may have a thickness smaller than 4 mm, such as smaller than 2 mm, such as smaller than 1 mm.

The wall sections of the rebreathing air chamber may comprise a polymer membrane, preferably comprising polytetrafluoroethylene (PTFE), perfluoroalkoxy (PFA), fluorinated ethylene propylene (FEP), polyvinylidene difluoride (PVDF), polyethylene (PE), polypropylene (PP), paper, vegetable fibres and/or combinations comprising any of the above-mentioned polymers.

In another embodiment (not shown in the figures) the through-going openings are arranged in the wall of the breathing channel and/or in the wall member 7.

In another embodiment (not shown in the figures) one or more of the through-going openings 8 may be re-closable and/or adjustable in size. These through-going openings may be re-closable and/or adjustable in size, e.g. by a valve mechanism, so the user can adjust the flow of air into and/or out of the breathing device, by closing or opening some of the through-going openings manually.

During use, the user breathes into/through the mouthpiece 2 through the breathing opening 5. A part of the expired flow from the user enters the rebreathing air chamber 6 and the rest enters the atmosphere through the through-going openings 8. When the user inhales, the air collected in the rebreathing air chamber 6 is re-inspired along with some fresh air entering from the atmosphere through the through-going openings, reducing the amount of inspired fresh air per minute (the alveolar ventilation) compared to when the user is not using the device. The ratio A/B is denoted the Rebreathing Ratio (RBR), A being the subset of the inspired air flow consisting of gas which has previously been breathed out and B being the total inspired air flow.

Alternatively, the amount of inspired "bag air" (air from the rebreathing air chamber 6) divided by the total ventilation (total ventilation=inspired bag air+inspired fresh air) may be defined as the Rebreathing Ratio (RBR).

The through-going openings 8 has a first conductance $G_{out}$ and the rebreathing air chamber 6 is impermeable to gas and has a second conductance $G_{expand}$, preferably defined as the volume expansion per second of the rebreathing chamber divided by the pressure difference between the inside the rebreathing air chamber and the surrounding atmosphere. The through-goings openings 8 and the rebreathing air chamber 6 are configured to provide a RBR defined as $RBR=G_{expand}/(G_{out}+G_{expand})$ between 0.2 and 0.65 or may be between 0.5 and 0.95.

The rebreathing air chamber 6 may be formed by one the following forms: cube, such as cuboid, sphere, such as spheroid, bag type, tetrahedron, such as substantially tetrahedron, square-based pyramid such as substantially pyramid, octahedron, such as substantially octahedron, hexagonal prism such as substantially prism, dodecahedron, such as substantially dodecahedron, cylinder, or cylindroid. The basic idea is to minimize the distance from the breathing channel to any point on the wall of the rebreathing air chamber.

In a preferred embodiment of the present invention, the rebreathing air chamber 6 in the form of a cube, such as a cuboid and is self-contained when formed. By self-contained is preferably meant that it maintains its shape by itself, e.g. without need of an extending overpressure to maintain its shape. The cube, such as cuboid shape, is formed when the user inflates the rebreathing air chamber.

The rebreathing air chamber 6 may comprise a valve for draining off condensed water (not shown in figures).

During use, no matter how the rebreathing air chamber is changed in shape, it must, without external impact, maintain the new shape without losing more than 50% of the inner volume due to the stress/elasticity of the panels of the rebreathing air chamber or the gravitational pull.

Figure 2:
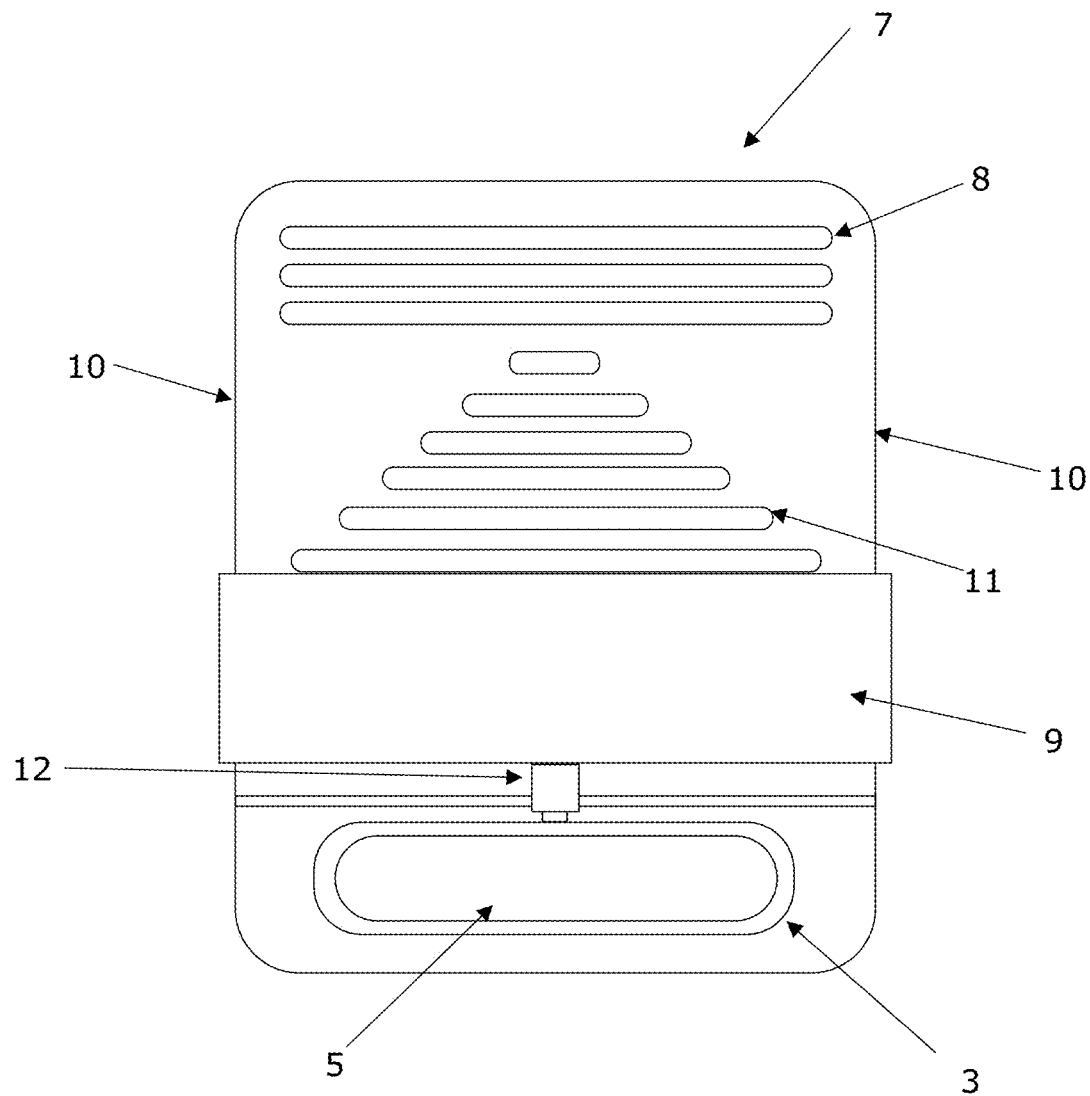
FIG. 2 schematically illustrates a wall member comprising through-going openings and a slider and a breathing opening of a mouthpiece.

Reference is made to FIG. 2, illustrating the wall member 7, the first end 3 of the mouthpiece 2 and the breathing opening 5. In FIG. 2 the rebreathing air chamber 6 is not shown.

In the embodiment shown in FIG. 2, the wall element 7 comprises three non-adjustable through-going openings 8, allowing fluid communication in and/or out of the rebreathing air chamber with the surrounding atmosphere, and six through-going openings 11. The through-going openings are in the form of longitudinal vent holes 8, 11 extending horizontally between the wall sections 10.

In FIG. 2 the through-going-openings 8, 11 are illustrated as having a longitudinal shape, however the through-going openings 8, 11 may be in rectangular and/or elliptical form, a round or roundly shape, or a combination of the above.

The longitudinal vent holes may in another embodiment extend vertically between the wall sections 10.

The wall element 7 further comprises a slider 9 configured for covering a portion of the longitudinal vent holes 11 provided on the wall member 7. The slider 9 is arranged between two parallel longitudinal wall sections 10. The slider provides an opening into the rebreathing air chamber 6 when moved by the user. In the embodiment shown in FIG. 2, the user may adjust the flow of air into the rebreathing air chamber 6 by moving the slider a distance to cover a portion of the six longitudinal vent holes 11. The slider cannot cover the three going-openings 8. This is typically provided by a stop mechanism preventing a user from advancing the slider 9 to cover the openings 8. However, the size of the slider 9 is furthermore sufficiently small that if it is advanced to cover the through-going openings 8, at least some of the vent holes 11 will be uncovered. Thereby, the user is prevented from suffocation since some opening(s) will always be uncovered. The slider 9 is configured for adjusting the flow of air into and/or out of the rebreathing air chamber 6 and the RBR ratio.

In an embodiment wherein the through-going openings are arranged in the wall of the breathing channel (not shown in the figures), a slider is arranged in the mouthpiece, for adjusting the flow of air in and/or out of the breathing channel by covering/uncovering a portion of the through-going openings, and hereby the flow of air into and/or out of rebreathing air chamber 6 and the RBR ratio.

In the embodiment shown in FIG. 2, the longitudinal vent holes 11 have an increasing length to provide stepwise and linear pressure drop increments when the slider 9 is moved from a first position to a second position.

Figure 5:
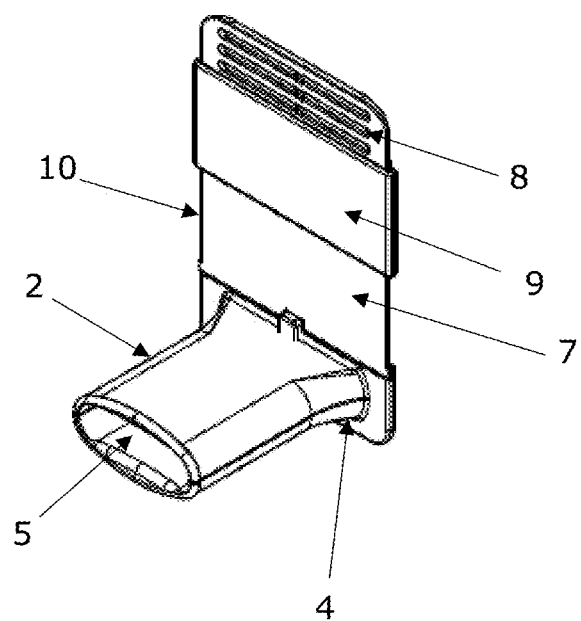
FIG. 5 schematically illustrates a wall member comprising through-going openings and a slider covering a part of the through-going openings.

By first position is meant a fully closed position of the slider 9 (all six longitudinal vent holes 11 are covered by the slider 9, enabling a minimal fluid communication between the rebreathing air chamber 6 and the surrounding atmosphere). FIG. schematically illustrates the wall member 7 and mouthpiece 2. In FIG. 5 the slider 9 is arranged in the first positon, covering the six longitudinal vent holes 11. Only the three through-going openings 8 are uncovered and visible in FIG. 5.

Figure 4:
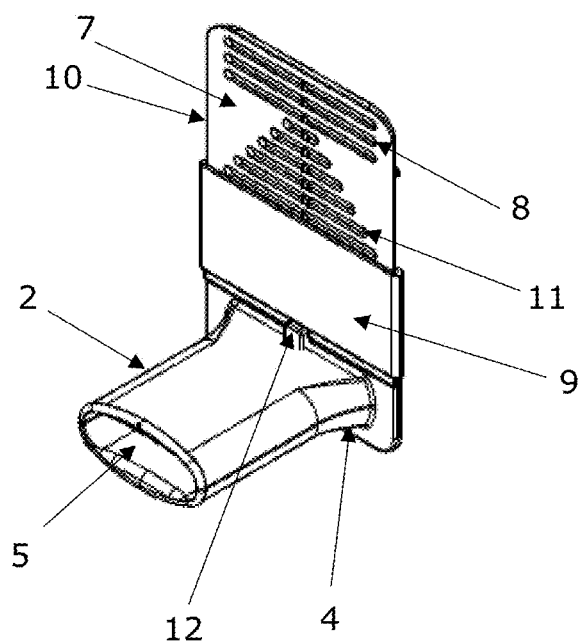
FIG. 4 schematically illustrates a wall member comprising through-going openings and a slider and a mouthpiece.

By second positon is meant a fully open position of the slider 9 (all six longitudinal vent holes 11 are un-covered by the slider enabling a maximum fluid communication between the rebreathing air chamber and the surrounding atmosphere). The increasing length of the longitudinal vent holes ensures that the magnitude of each incremental change in total flow resistance is approximately equal (i.e. when the slider is moved incrementally from the first to the second position or vice-versa). FIG. 4 schematically illustrates the wall member 7 and mouthpiece 2. In FIG. 4 the slider 9 is arranged in the second positon, not covering any of the six longitudinal vent holes 11. All three through-going openings 8 and six longitudinal vent holes 11 are uncovered and visible in FIG. 4.

The user can move the slider so as to cover one, two, three, four, five or six of the longitudinal vent holes 11, depending on the desired flow of air into and/or out of the rebreathing air chamber 6 and on the desired RBR ratio.

Figure 3:
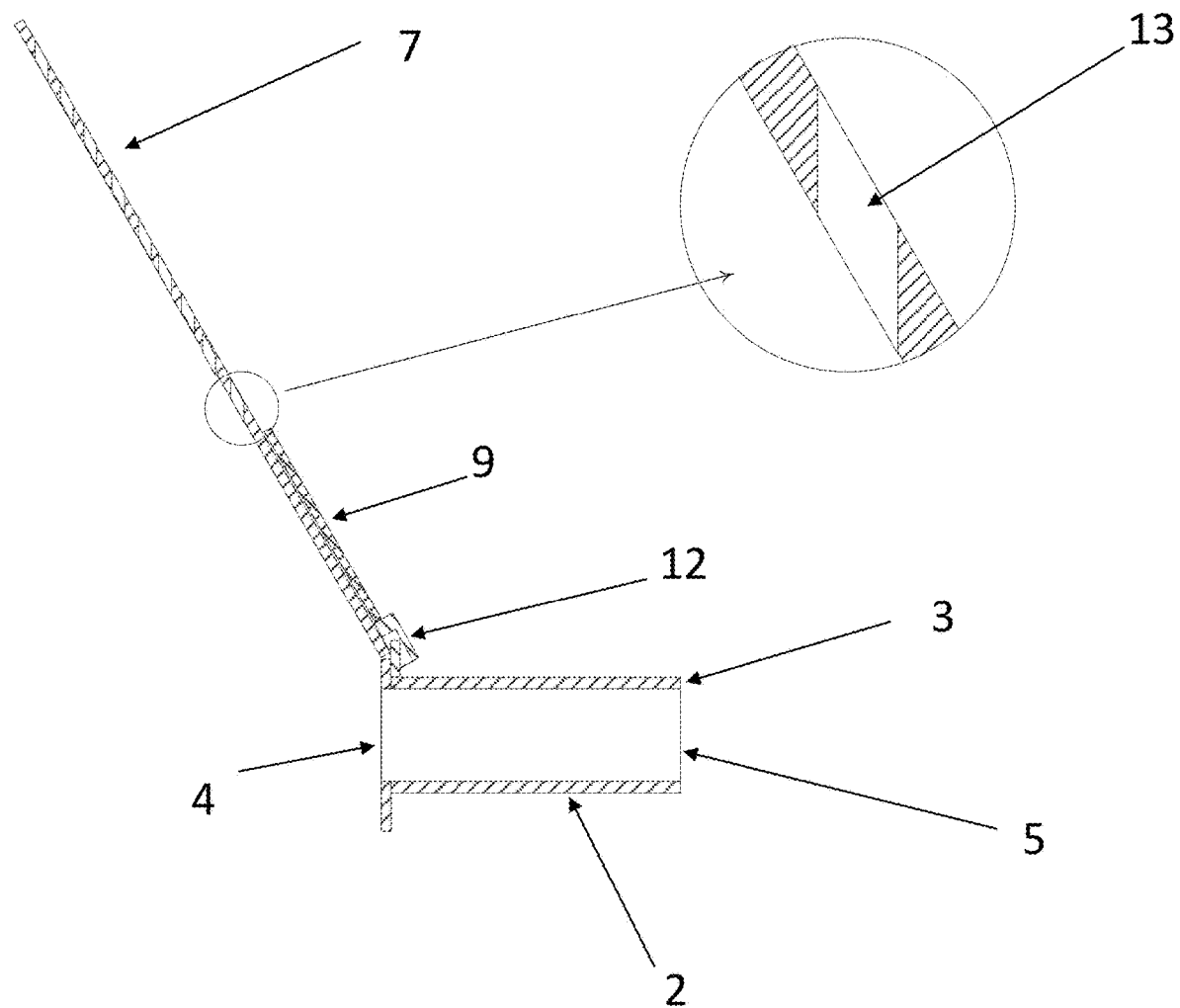
FIG. 3 schematically illustrates a wall member, slider and a mouthpiece from a side view and as a cross sectional view.

Reference is made to FIG. 3, illustrating the wall member 7, the mouthpiece 2 and the slider 9 from a side view and as a cross sectional view.

Figure 6:
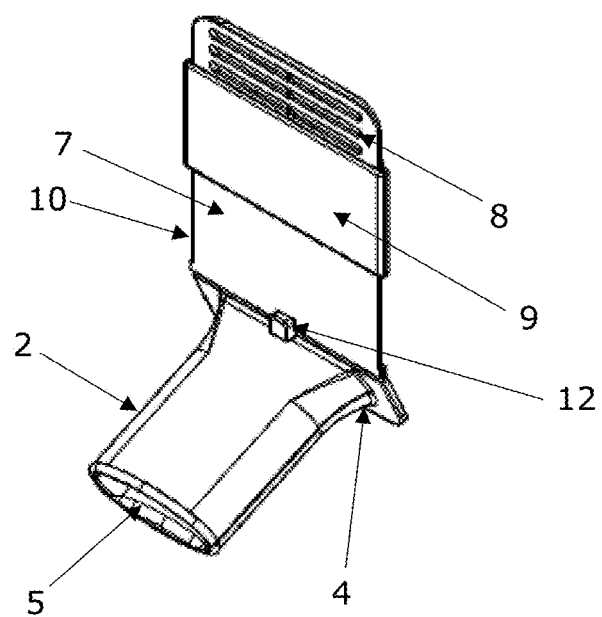
FIG. 6 schematically illustrates a wall member displaced with an angle relatively to a mouthpiece.
Figure 7:
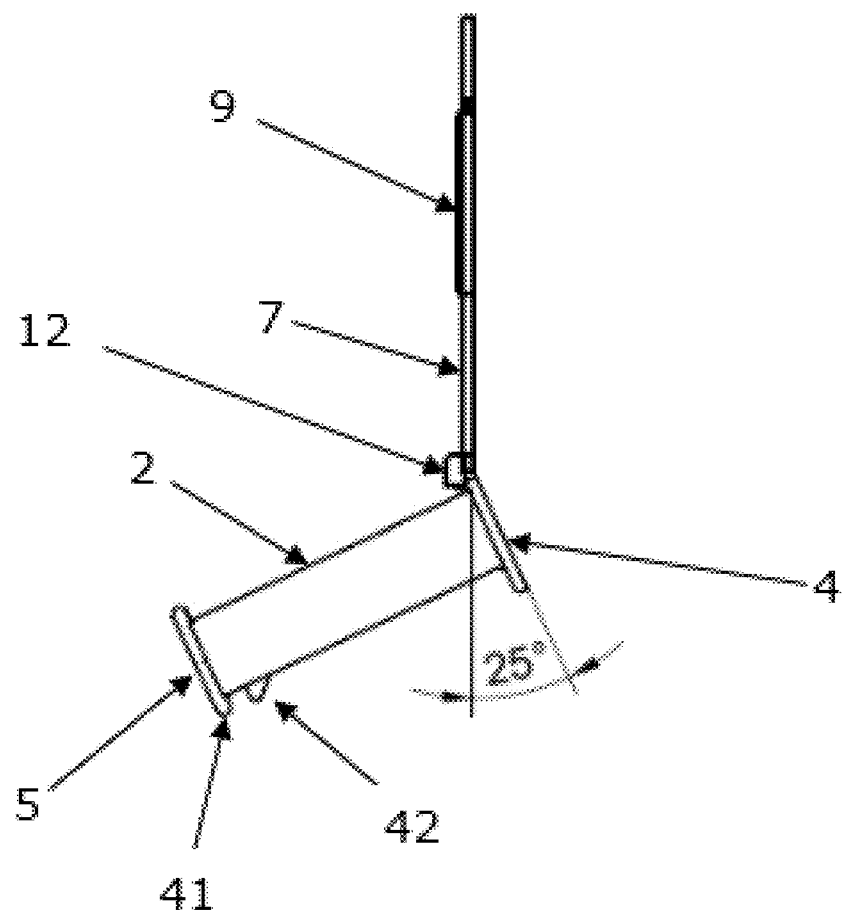
FIG. 7 schematically illustrates a wall member displaced with an angle relatively to a mouthpiece from a side view.

The wall member 7 is pivotally connected to the mouth piece 2 and the connection comprises a latch 12, configured for adjusting an angle between the wall member 7 and the mouthpiece 2, in order to avoid exterior gas from the rebreathing air chamber impacting on the user's face with enough force to be noticeable by the user. The angle between the wall member 7 and the mouthpiece 2 also enables the user to have a clear view over the rebreathing air chamber during use. The angle also increases the distance from the wall member 7 to the users face and nose, as it is uncomfortable that the wall member 7 is very close to the users face and nose. Users with bigger noses will also benefit of this increased distance, so as not touching the wall member 7 with the nose. FIG. 6 illustrates the wall member 7 displacement relative to the mouthpiece 2. FIG. 7 illustrates a side view of the wall member being displaced with an angle of 25 degrees relative to the mouthpiece 2.

Also illustrated in the embodiment shown in FIG. 7 is a teeth-support arrangement which can be used to "hang" the device in the teeth of a user. The teeth-support comprising a ridge 41 arranged at the first end 3 and encircling the breathing opening 5. To assist in the hanging, a traversing projection 42 may be arranged slightly distant (to allow for accommodation of teeth) from the ridge 41 on a lower surface of the mouth piece 2 (lower refers to the orientation shown in the figure). Alternatively, the traversing projection 42 may be arranged on the upper surface or on both upper and lower surface of the mouth piece 2.

In FIG. 3, the longitudinal vent holes 8, 11 are of oblique shape 13, meaning that the vent holes proceed through the wall member 7 in an oblique manner relative to the orientation of the plane defined by the wall member. This is illustrated in FIG. 3 by a close-up view of an obliquely shaped vent hole 13.

Figure 9:
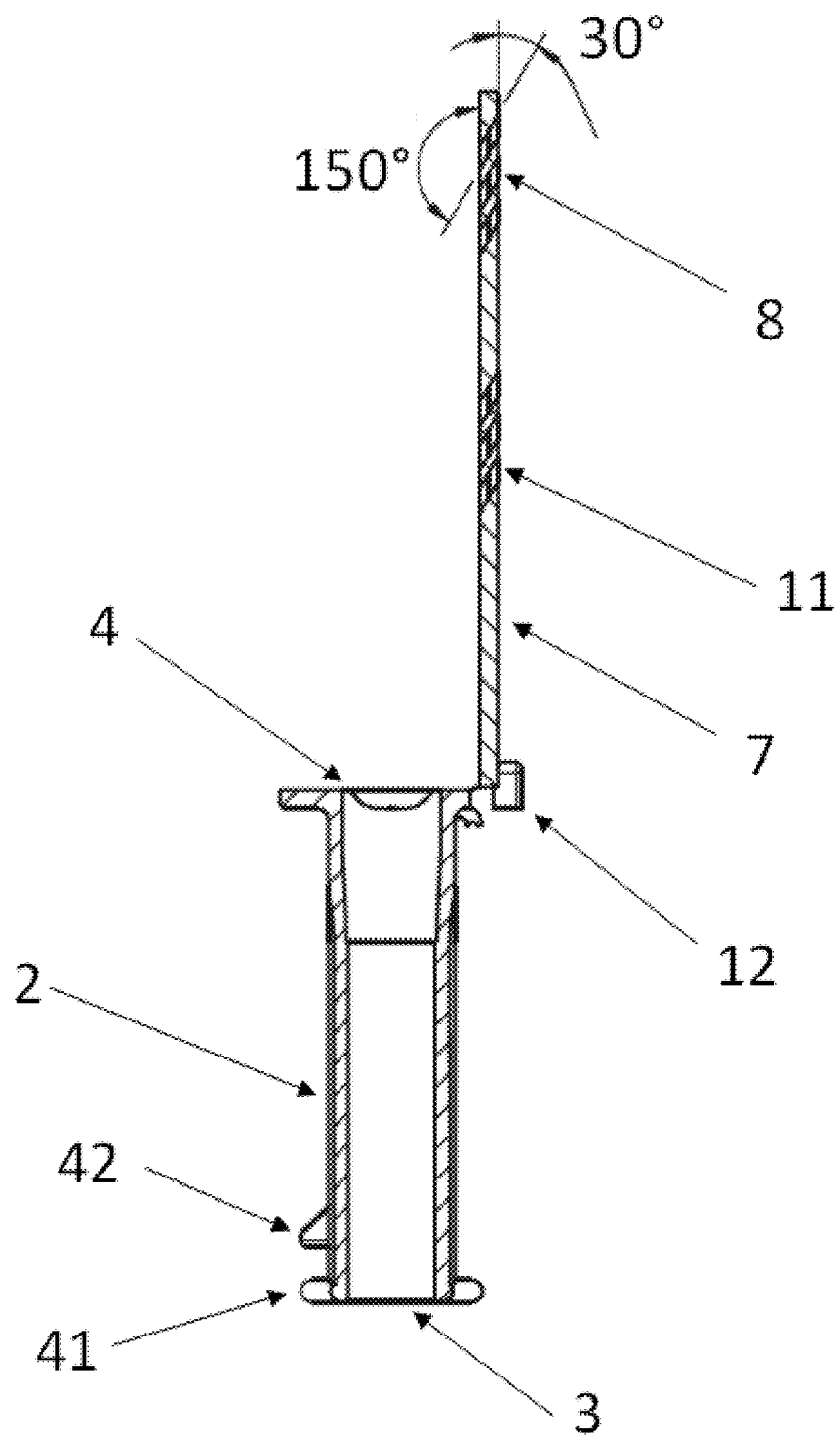
FIG. 9 schematically illustrates a wall member comprising through-going openings proceeding through the wall member in an oblique manner.

In an embodiment of the present invention, the vent holes proceed through the wall in an angle of 10-80 degrees, such as 20-70 degrees, preferably 60 degrees. This is schematically illustrated in FIG. 9, where the vent holes proceed through the wall in an angle of 30 degrees. The vent holes are configured for providing a guided directional outflow outside the breathing device 1 away from the users face.

In another embodiment (not shown in the figures), the angle of the vent holes through the wall may be sufficient to guide the directional outflow outside the breathing device 1 away from the user's face, hence the wall member in this embodiment does not comprise a latch for adjusting an angle between the wall member 7 and the mouthpiece 2.

Figure 8:
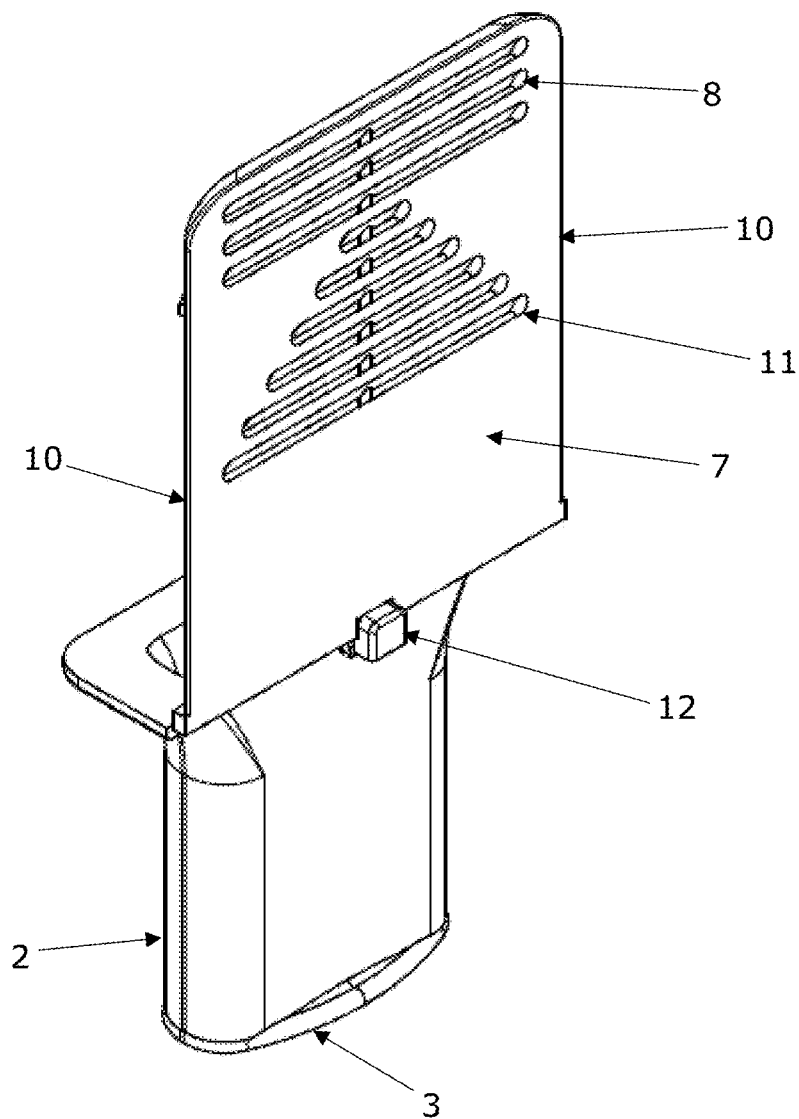
FIG. 8 schematically illustrates a wall member comprising through-going openings and a mouthpiece.

FIG. 8 schematically illustrates the wall member 7 and the mouthpiece 2. In FIG. 8 the wall member 7 is arranged 90 degrees relatively to the second end 4 of the mouthpiece 2.

In another embodiment, the breathing device 1 further comprises a SpO2-sensor (not shown), configured for measuring the oxygen level of the user's blood, and/or a side-inlet arranged in the mouth piece 2. The side-inlet being arranged so as to extract a portion of the air flowing through the breathing channel, preferably for forwarding the extracted air to a $CO_2$ determining device, so as to determine the $CO_2$ level of the user's exhaled breath via the extracted air. The amount of air extracted is negligible, so it has no influence on the RBR of the breathing device.

The measurement of the oxygen level of the user's blood is measured preferably optically through the surface of the user's skin, and requires no medically trained personnel's interaction. The SpO2 and/or $CO_2$ sensor may be an integrated part of the breathing device or an external part. Such sensors can be used to monitor whether the $CO_2$ exceeds or falls below a certain limit and/or the 02 level is below a certain limit and if either of these situations occurs, a warning may be signalled to the user.

In another aspect, the invention relates to a kit of parts for increasing and/or balancing and/or maintaining a specific level of $CO_2$ in the inhaled air, comprising a breathing device, a SpO2-sensor and a nose clip. The desired specific level of $CO_2$ in the inhaled air is different for each user.

In a third aspect, the present invention relates to a method for adjusting the RBR. The method utilizes a breathing device with an adjustable RBR and a computer configured to automatically determine whether to change the RBR based on a user's response to a questionnaire. The RBR is changed via a setting of the slider's position, each setting corresponding to a specific position of the slider 9 on the wall element to cover a portion of the longitudinal vent holes 11. The method comprises the steps of:

providing measurement(s) of a user's blood oxygen level and/or CO2 level in exhaled air by use of a SpO2-sensor and/or $CO_2$ sensor, executing a questionnaire containing questions relating the user's response to the use of the breathing device during use of the breathing device, in response thereto determining by use of the computer whether to change the RBR, and if the RBR is determined to be changed, signalling to the user a new setting for the breathing device.

The method may also take into account the user's GPS position (e.g. if the user is on a mountain where the air density is low) as well as iHealth information, previous changes in the RBR, or other user data such as gender, age, type of disease etc.

The computer (not shown in the figures) is configured to automatically determine whether to change the RBR based on a user's response to a questionnaire. The computer signals to the user a new setting for the breathing device (an adjustment of the breathing device's RBR by moving the slider to a specific position on the wall member, covering a portion of the longitudinal vent holes 11, or e.g. moving the slider to a first or second position).

The computer may be a smartphone or a tablet. The computer has a number of pre-stored baseline settings, each setting corresponding to a slider position. A baseline setting may be a setting corresponding to an advisable device configuration for first time use, which setting may be ruled by a number of parameters, such as age, gender etc.

Figure 10:
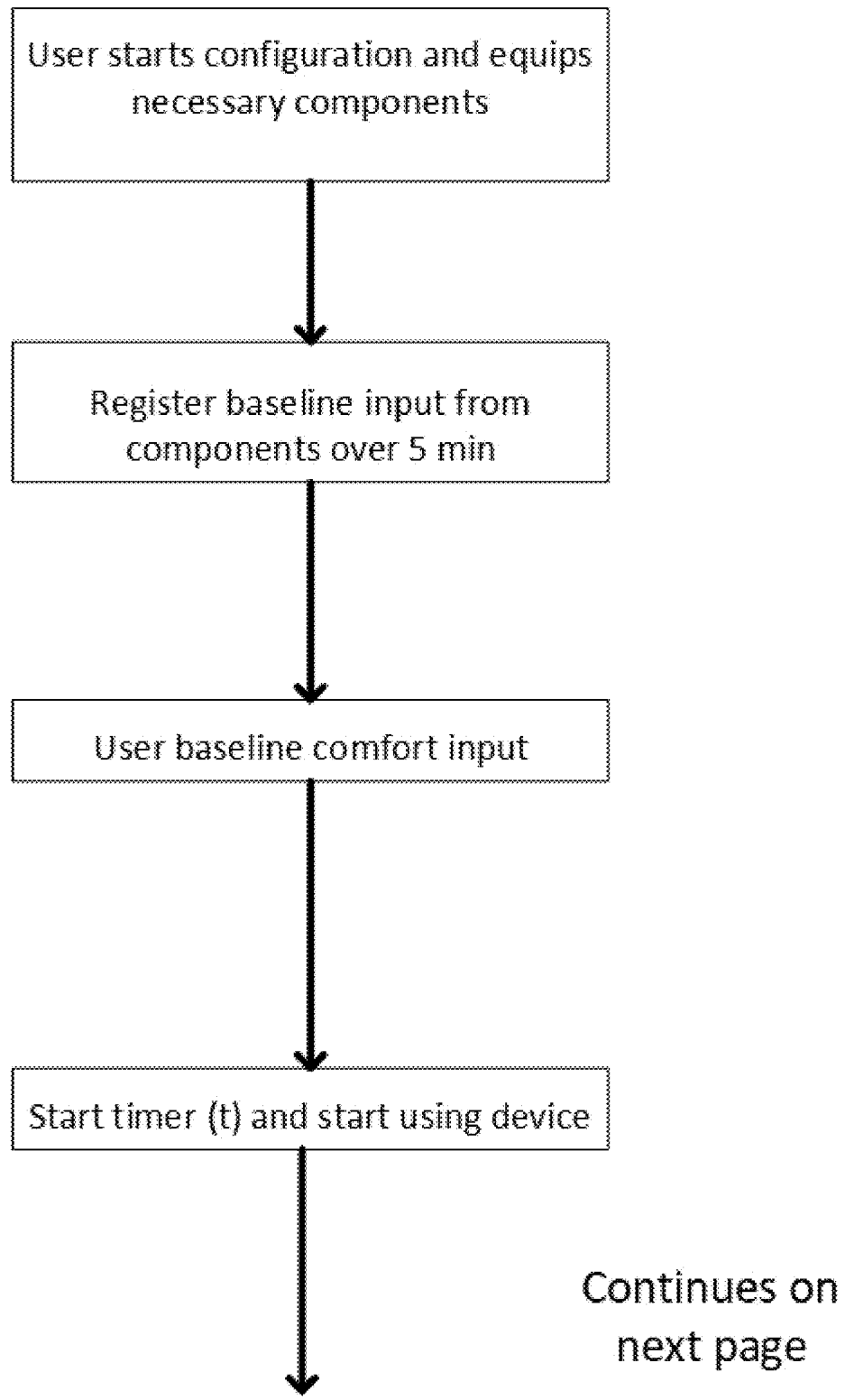
FIG. 10 is a flow-chart of a method according to the present invention.
Figure 10:
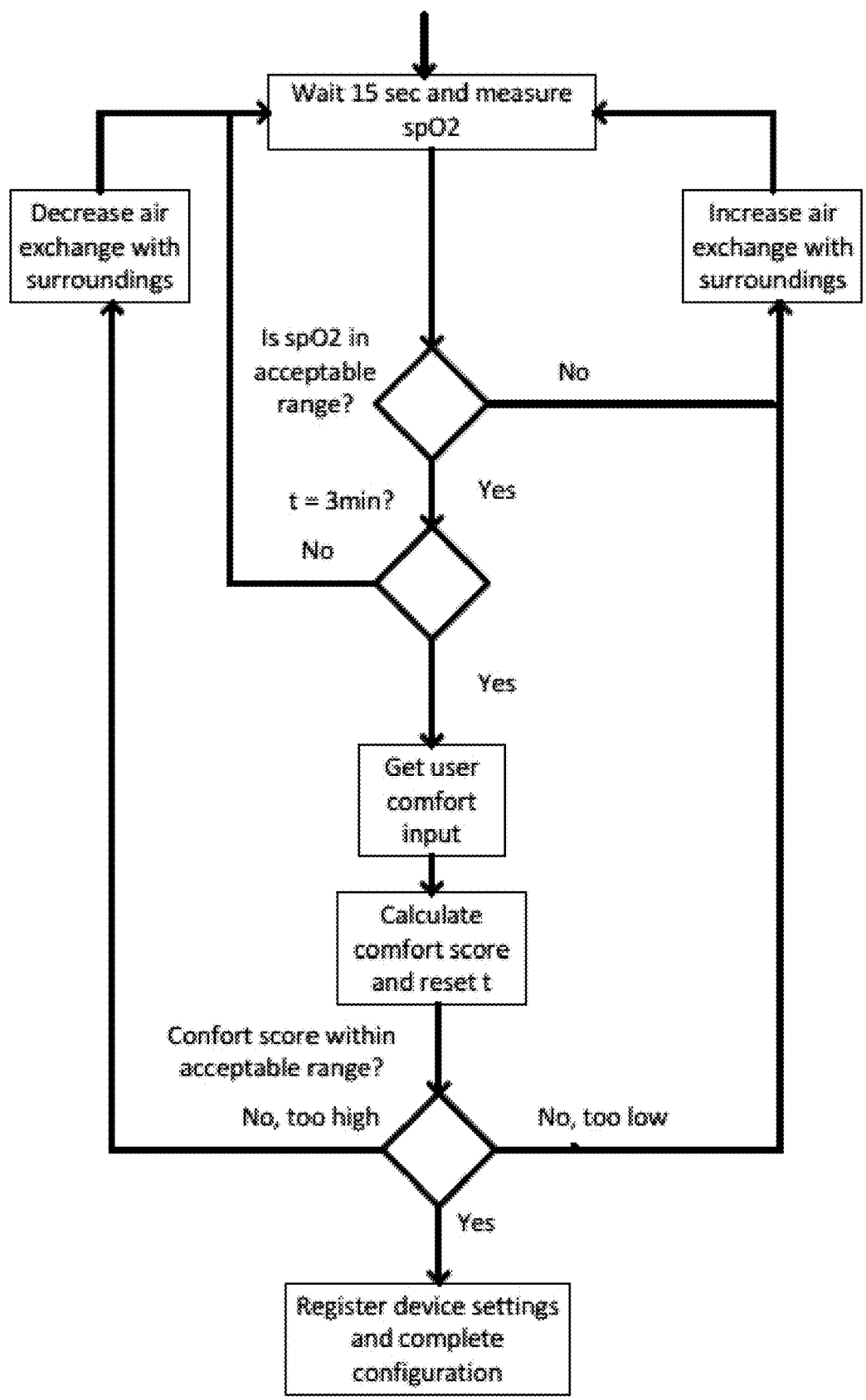

A flowchart describing the method for adjusting the RBR is illustrated in FIG. 10. The flowchart contains the steps required in a software application to perform the method according to the present invention.

Starting from the top of the flowchart, the following steps are followed, according to the flow chart (FIG. 10):

1: The user starts by "unpacking" the kits of parts e.g. the breathing device and the SpO2 sensor and/or CO2 sensor and installing an application, containing the required software, on e.g. a mobile phone.

2: Before suffering from an acute problem, such as during a migraine attack, the user measures the level of oxygen in the blood by use of the SpO2 sensor in a time period of 5 minutes. If a CO2 sensor is part of the kit of parts, CO2 measurement of the exhaled air is also done in this period

3: The application retrieves the data from the SpO2 and/or $CO_2$ measurements.

4: The application executes a questionnaire containing questions relating to the user's wellbeing prior to the use of the breathing device. The questions may be:

How do you feel right now? (0, 1, 2, 3, 4, 5, 6, 7, 8, 9, 10)

Pain in the head/neck? (no, little, in between, very)

Pressure in the head/neck? (no, little, in between, very)

Tired? (no, little, in between, much)

Dizziness? (no, little, in between, very)
Nausea? (no, little, in between, very)
Heavy breathing? (no, little, medium, much)
Warm in the face or body? (no, little, medium, very)
The breathing is faster and deeper? (no, little, medium, much)
Hard to concentrate? (no, little, in between, much)
I feel uncomfortable? (no, little, in between, very)

In the above, the scale used is "no", "little", "in between" and, "much" or "very". An alternative scale used in connection with the present invention is "no", "a little", "medium" and "a lot".

Some of the answers are given on a numerical scale (e.g. 0 to 10) and others on a semi-quantitative scale (e.g.: no, a little, medium, a lot).

5: The user starts to breathe through the breathing device and a timer is started.

6: After 15 seconds the application initiates a measurement of the SpO2 and/or CO2 level.

7: If the oxygen level of the blood is not at the desired value, the application signalizes to the user that the amount of fresh air exchanged with the surrounding atmosphere must be increased; meaning that the slider must be changed to a position on the wall member 7 (or changing the position of the slider on the mouthpiece if the through-going openings are arranged in the wall of the breathing channel) to uncover a portion of the longitudinal vent holes 11 and hereby decreasing the value of the RBR.

8: Again, after 15 seconds the application initiates a measurement of the SpO2 level and/or CO2 level.

9: If the oxygen level of the blood is still not at the desired value, then the sub-steps in step 7 are executed again.

10: When the timer started in step 5 is at 3 minutes continue to step 11.

11: The application executes a questionnaire containing questions relating to the user's wellbeing while using the breathing device. The questions may be:
How do you feel right now? (0, 1, 2, 3, 4, 5, 6, 7, 8, 9, 10)
Pain in the head/neck? (no, little, in between, very)
Pressure in the head/neck? (no, little, in between, very)
Tired? (no, little, in between, much)
Dizziness? (no, little, in between, very)
Nausea? (no, little, in between, very)
Heavy breathing? (no, little, medium, much)
Warm in the face or body? (no, little, medium, very)
The breathing is faster and deeper? (no, little, medium, much)
Hard to concentrate? (no, little, in between, much)
I feel uncomfortable? (no, little, in between, very)

As above, the scale used is "no", "little", "in between" and, "much" or "very". An alternative scale used in connection with the present invention is "no", "a little", "medium" and "a lot".

Some of the answers are given on a numerical scale (e.g. 0 to 10) and others on a semi-quantitative scale (e.g.: no, a little, medium, a lot).

12: The application then uses a combination of the answered questionnaire compared to the initial pre-use questionnaire answers, the SpO2 and/or $CO_2$ levels, information about the previous changes to the slider information, previously calculated "comfort" scores as well as general information from the computer/smartphone such as health, fitness and GPS, to calculate a "comfort" score that indicates whether the user is in the correct treatment window.

13: If the "comfort" score is over a certain value, the user is not affected enough by the $CO_2$ and is therefore outside the desired treatment window. The application therefore signalizes to the user that the amount of fresh air exchanged to the surrounding atmosphere must be decreased; meaning that the slider must be changed to a position on the wall member 7 (or changing the position of the slider on the mouthpiece if the through-going openings are arranged in the wall of the breathing channel) to cover more of the longitudinal vent holes 11 and hereby increase the value of the RBR. After the slider setting change, the timer is reset and the configuration process restarts from step 6.

14: If the "comfort" score is lower than a certain value, the user is too affected by the $CO_2$ and is therefore outside the desired treatment window. The application signalizes to the user that the amount of fresh air exchanged to the surrounding atmosphere must be increased; meaning that the slider must be changed to a position on the wall member 7 (or changing the position of the slider on the mouthpiece if the through-going openings are arranged in the wall of the breathing channel) to uncover more of the longitudinal vent holes 11 and hereby decreasing the value of the RBR. After the slider change, the timer is reset and the configuration process restarts from step 6.

15: If the "comfort" score is within an acceptable range, the application registers the settings (the position of the slider) and the configuration is completed.

When at a subsequent time the user needs to use the breathing device, the slider setting found during the configuration process (step 1-15) can be retrieved by the app and communicated to the patient so that he/she will know where to set the slider to be in the correct treatment window, without having to go through steps 1-15 again.

The configuration can be more finely tuned to the individual user through a treatment plan where the user interacts with the system in a very similar flow as step 1-15, but while the user is actually suffering from an acute problem such as during a migraine attack. This treatment plan can vary in length and complexity, but involves multiple data inputs over a longer period of time and during multiple acute illness situations such as migraine attacks, etc. This will eventually help the system to determine the best treatment settings and timings for the individual user.

The breathing device, according to any of the embodiments mentioned, may be used in the treatment of migraine, epilepsy, febrile seizures, post-spinal headache, and asthma and in general to raise the bodily $CO_2$ levels and lower the pH values of the bodily fluids.

The individual elements of an embodiment of the invention may be physically, functionally and logically implemented in any suitable way such as in a single unit, in a plurality of units or as part of separate functional units. The invention may be implemented in a single unit, or be both physically and functionally distributed between different units and processors.

Figure 11:
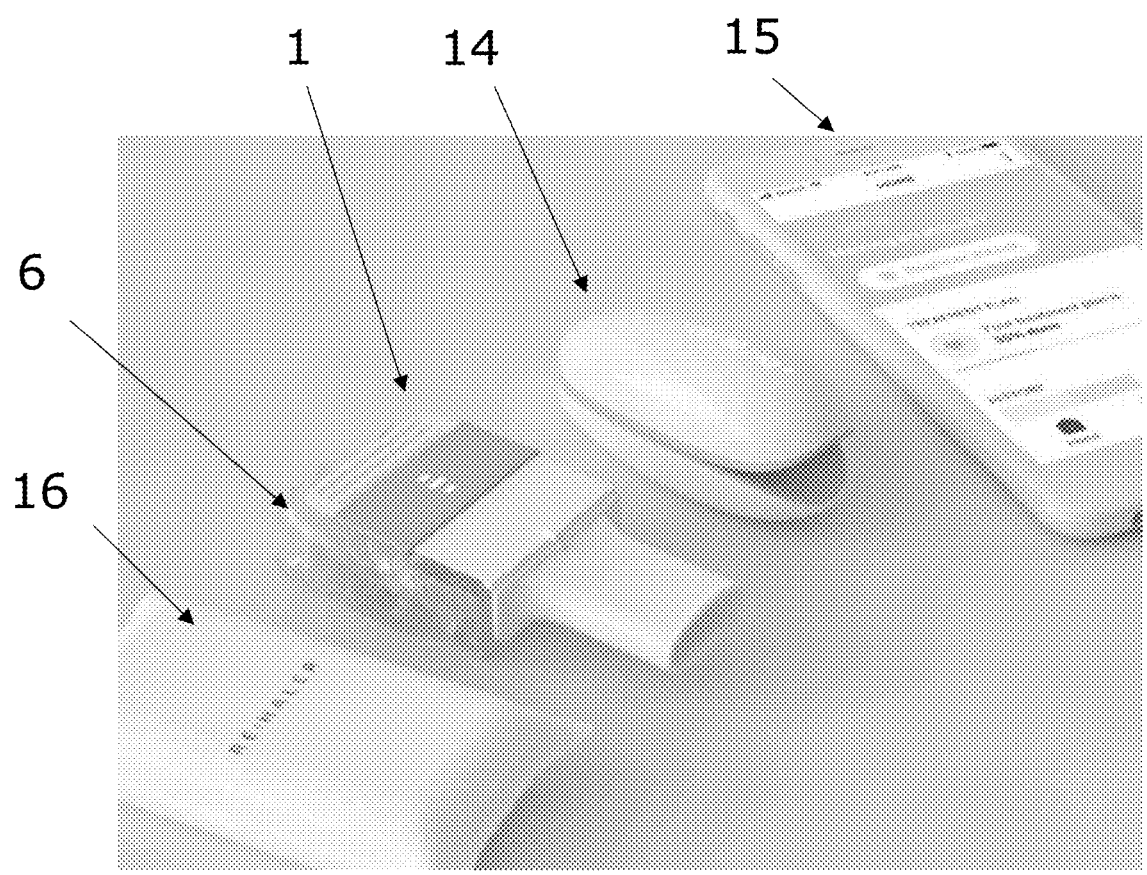
FIG. 11 is a photograph illustrating various parts of the invention.

Reference is made to FIG. 11 being a photograph illustrating a preferred embodiment of a packaging 16 containing a preferred embodiment of a breathing device 1. The packaging 16 is preferably made as a bag-like structure into which the breathing device 1 as shown in FIG. 11 is introduced. The packaging 16 is typically sealed to prevent contamination of the breathing device while being contained in the packaging. In some embodiments, the packaging is made from heat weld-able plastic material and the packaging is sealed by heat welding.

As illustrated in FIG. 11, the rebreathing air chamber 6 is folded (unfolded configuration may be as illustrated e.g. in connection with FIG. 1). As illustrated, the outer geometry of the folded chamber 6 is of comparable size to the wall section 10, so that the outer geometry packed breathing device 1 is kept small. The wall member 7 is in the position as illustrated in FIG. 9. Thus, the breathing device shown in FIG. 11 may be seen as being in a folded configuration.

FIG. 11 also shows a preferred embodiment of sensor 14—an SpO2 sensor—for measuring the oxygen level in blood. The device illustrated is of a type configured to be applied on e.g. a person's finger by introducing the finger into the opening shown.

FIG. 11 also shows a portable electronic device 15 (a computer in general)—in the photograph embodied as a smartphone. The smartphone has an application configured to carry one or more of the methods disclosed herein, such as the method disclosed in connection with FIG. 10. Preferably, to provide the user with a personalized care scheme. The sensor 14 may be configured to communicate readings obtained by the sensor directly, such as through wireless communication, to the smartphone 15.

The breathing device 1 and the sensor 14 may preferably form a kit of parts. In such kits of parts, the breathing device 1 may preferably be arranged in the packaging 16. Further such kits of parts may comprise a plurality of breathing devices 1, such as a plurality of breathing devices 1 each in a packaging 16, and a single sensor 14. The plurality may be 2, 3, 4, 5, 6, 7, 8, 9, 10, 11, 12 or even more.

The application is typically downloaded from a server. To this end, the packaging, e.g. may contain a bar code (or other information) readable by the smartphone and re-directing e.g. a browser to a web-site for download of the application.

Figure 12:
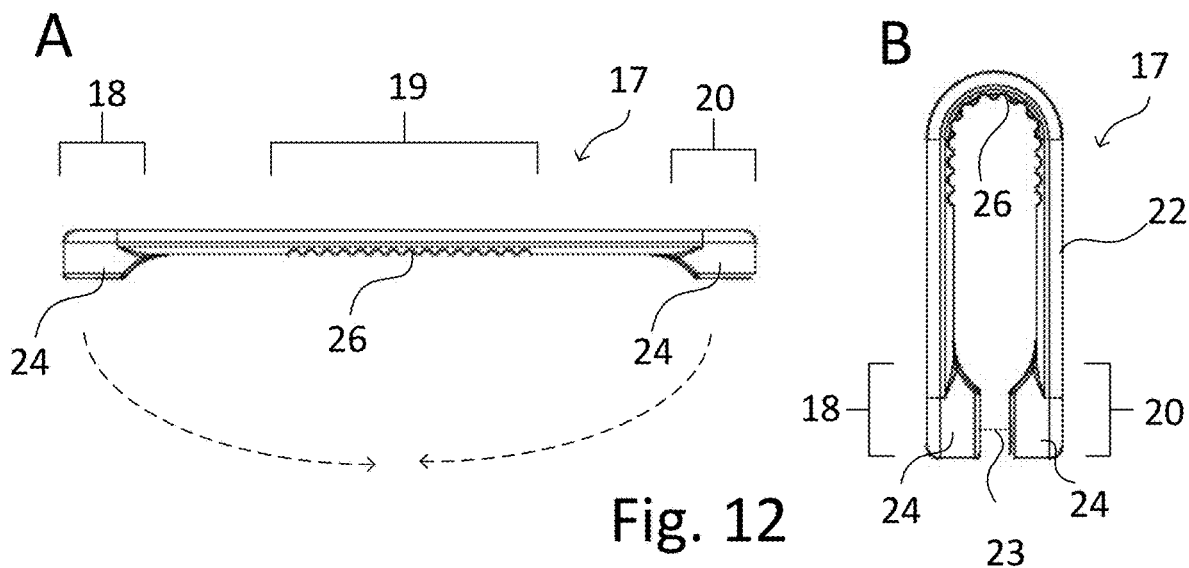
FIGS. 12, 13 and 14 illustrate a nose clamp according to a preferred embodiment of the present invention.
Figure 13:
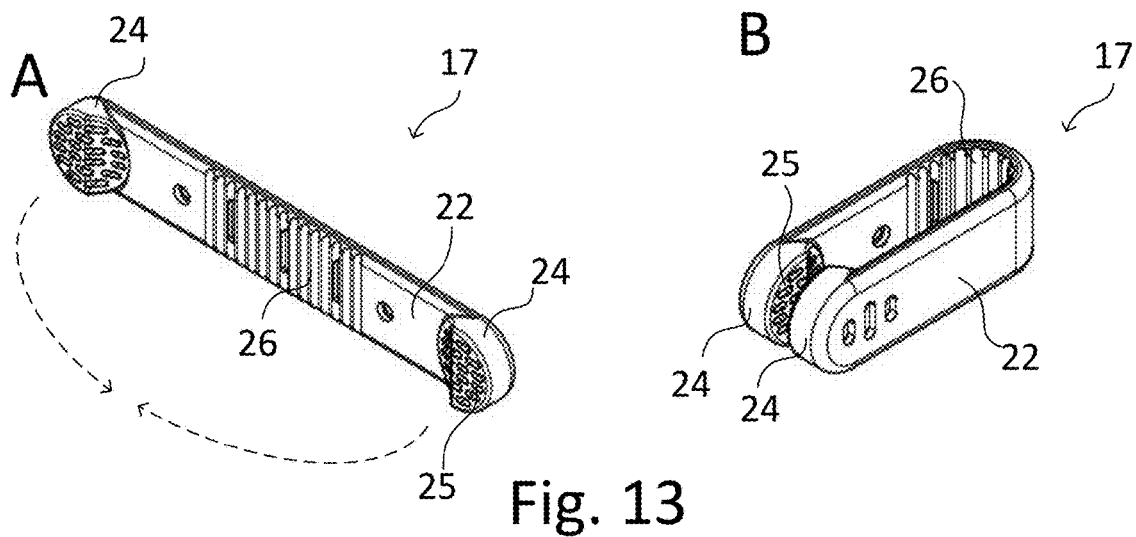

Reference is made to FIGS. 12 and 13 illustrating a nose clamp 17 according to a preferred embodiment of the present invention. FIG. 12 illustrates a side-view of the nose clamp 17 in a straight (12A) and a curved (12B) configuration, whereas FIG. 13 illustrates a three-dimensional view of the nose clamp in the straight (13A) and the curved configuration (13B).

The nose clamp 17 of the present invention is a portable nose clamp 17 configured to be manually applied to the nostrils of a user and to provide a pressure on the nostrils, until the user wishes to adjust the pressure or remove the nose clamp 17. However, due to the configuration of the nose clamp 17 of the present invention, the nostrils are not forced together as with other nose clamps. The perfect plasticity of the device, allows the nostrils to be closed, without causing discomfort for the user.

As illustrated in FIGS. 12 and 13, the nose clamp 17 of the present invention is an elongated element comprising a first end section 18, a mid-section 19 and a second end section 20. The nose clamp 17 of the present invention may be in a substantially straight configuration (12A and 13A) or in a more or less curved configuration (12B and 13B). If the nose clamp 17 is in the straight configuration, the curved configuration can be obtained by bending the first end section 18 and the second end section 20 of the nose clamp 17 toward each other to a desired extend, as illustrated by the dotted arrows in FIGS. 12A and 13A. If the nose clamp 17 is in a first curved configuration, a second curved configuration can be obtained by bending the first end section 18 and the second end section 20 of the nose clamp 17 further toward each other, to obtain a more curved configuration.

The first end section 18 and the second end section 20 can also be pulled away from each other, to obtain a less curved configuration. Thus, the space 23 between the first end section 18 and the second end section can be set as desired. The first end section 18 and the second end section 20 of the nose clamp 17 is configured to provide pressure on the nostrils. Depending on the space 23 between the first end section 18 and the second end section 20, more or less pressure may be applied to the nostrils.

Figure 14:
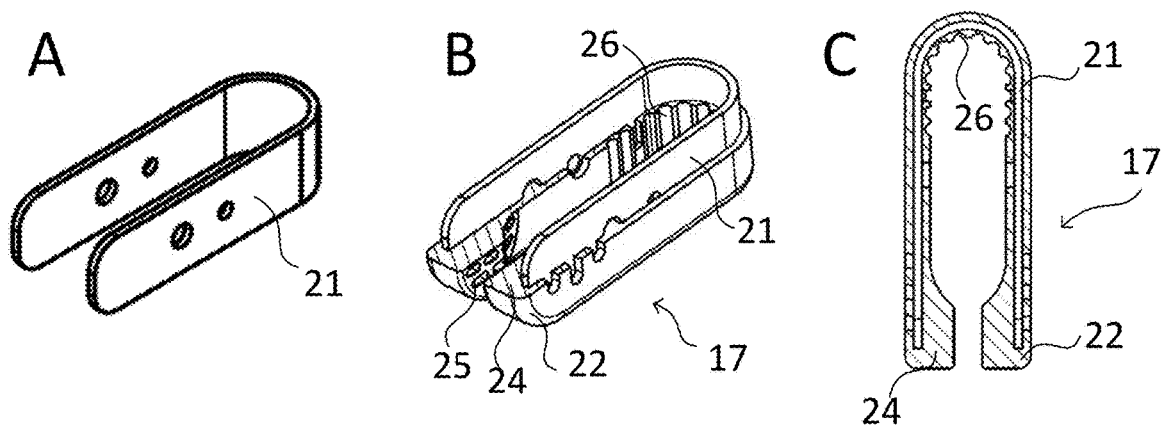

The nose clamp 17 of the present invention comprises an elongated aluminium strip 21, coated with a soft material, such as silicone, rubber, leather or thermoplastic elastomers (TPE). The coating 22 covers the aluminium strip 21 on all sides. Thus, the aluminium strip 21 is not visible in FIGS. 12 and 13 as it is located within the coating 22, but can be viewed in FIG. 14.

The aluminium strip 21 within the nose clamp 17 provides a pliability to the nose clamp, allowing it to be bent from a straight configuration to a curved configuration or from a first curved configuration to a second curved configuration. Furthermore, the aluminium strip 21 has a malleability allowing the nose clamp 17 to retain its shape when bended, until further manipulation. The adjustability of the nose clamp 17, allows it to be used on different nose sizes.

Preferably, the aluminium strip has a single thickness along the whole length. The thickness should be less than 1.0 mm, to allow the aluminium strip to be bended by a user.

Figure 22:
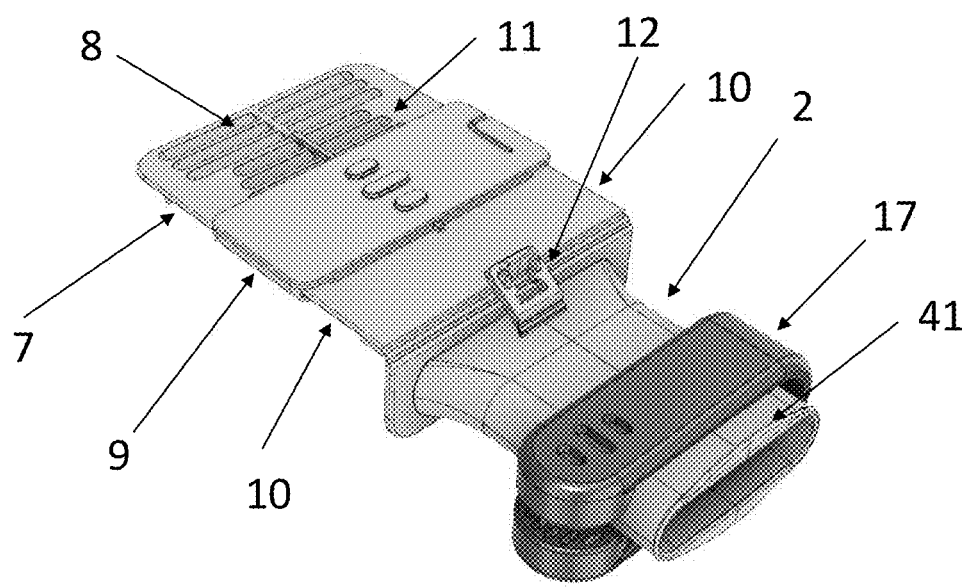
FIG. 22 is a illustration showing the nose clamp arranged on the mouth piece.

Reference is made to FIG. 22 which is an illustration showing the nose clamp 17 arranged on the mouth piece 2. The nose clamp 17 is bent into a configuration where the mouth piece 2 is accommodated in the space formed by the bending of the clamp; this configuration is shown in FIG. 12B. When a user is to use the nose clamp 17, the flexibility of the nose clamp 17 allows it to be released from the mouth piece 2.

The nose clamp is in some embodiments characterized by having an elastic limit between 1 and 10 newtons, the elastic limit here being defined as the minimum total inward forces $F_{compression}$ that must be applied to the end sections 18 and 20 when the nose clamp is in its curved configuration (FIGS. 12B and 13B) in order for the nose clamp to deform in a non-reversible, plastic (i.e. non-elastic) manner, this force being exerted inwards on the end sections in the direction shown by the arrows 28 (see FIG. 15) in such a way as to decrease the width of the space 23 between the protrusions 24.

Figure 15:
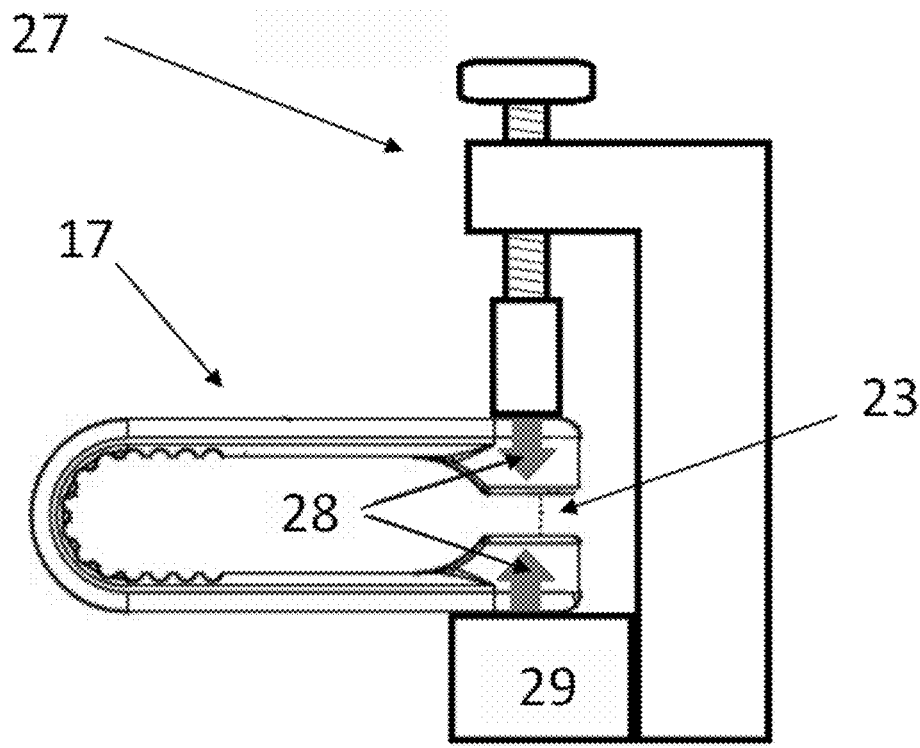

FIG. 15 shows an experimental setup for measuring the elastic limit of a nose clamp, in which the nose clamp is inserted in a vice that can be adjusted to exert a variable force. The bottom half of the vice consists of a digital weight scale 29. The total downwards force exerted on the nose clamp in a static situation can be calculated as $F_{down}=M \times g$, where M is the weight reading on the digital weight scale and g is the standard acceleration of gravity (9.81 m/s²). The total inwards-directed (i.e. compressing) forces on the nose clamp in a static situation is equal to $F_{compression}=2 \times F_{down}=2 \times M \times g$ because (cf. Newton's third law) the bottom half of the vice will exert a force on the nose clamp which is equal in magnitude but of opposite direction to $F_{down}$.

Figure 16:
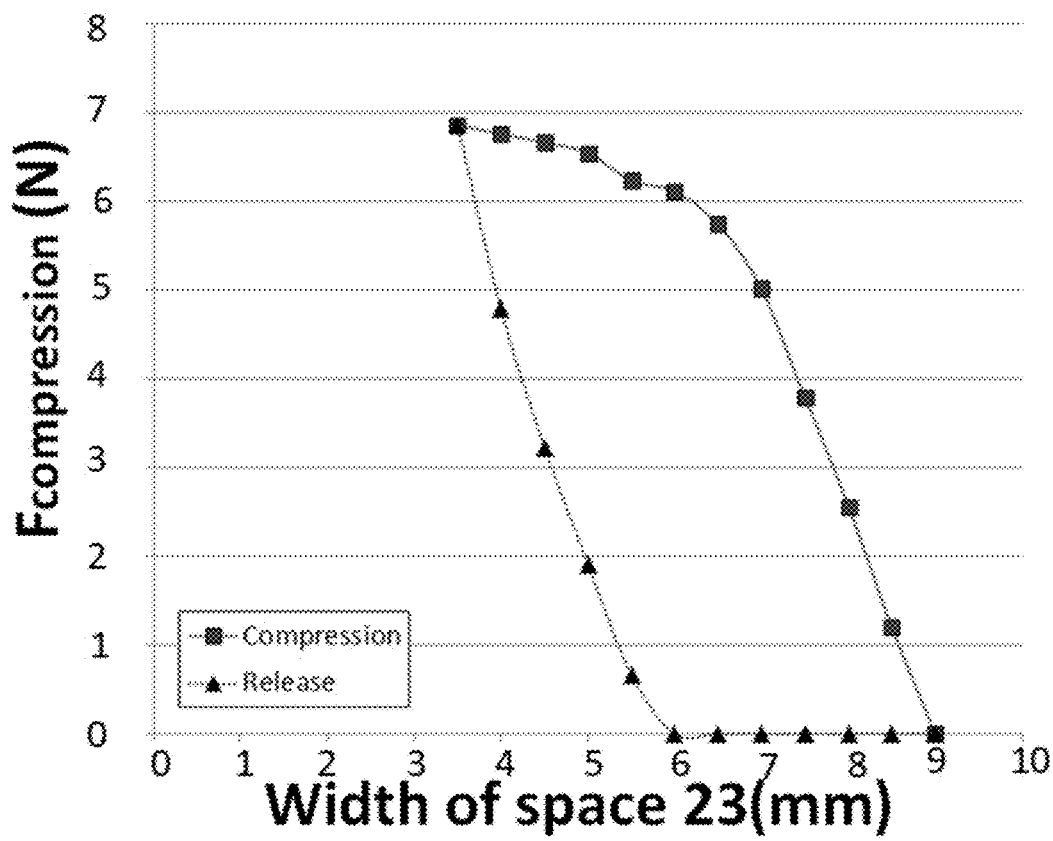
FIG. 16 is a graph illustrating compression force as function of width of space 23 of a nose clamp.

FIG. 16 shows a graph of a range of measurements of the width of the space 23 with corresponding values of $F_{compression}$ applied to the end sections 18 and 20 of the nose clamp 17 in one embodiment. In FIG. 16, the elastic limit can be identified as the force below which the gradient of the $F_{compression}$ curve is constant (i.e. the $F_{compression}$ curve is linear below the elastic limit), further increases in force above the elastic limit leading to non-elastic deformation.

Due to the soft coating 22, the nose clamp 17 of the present invention is comfortable for a user to wear. The coating material is preferably silicone or silicone rubber, rubber, leather, but may also be thermoplastic elastomers (TPE). Without the aluminium strip 21, the nose clamp 17 may not have a malleability allowing the nose clamp 17 to retain its shape when bended, until further manipulation.

As illustrated in FIGS. 12 and 13, the outer edges of the first end section 18 and the second end section 20 of the nose clamp 17 may be rounded. Furthermore, the first end section 18 and second end section 20 may each comprise a protrusion 24, being in the same material as the coating and/or formed integrally with the coating 22. The protrusions 24 act as small pillows, to provide comfortability to the user. Furthermore, the space 23 between the protrusions 24 allows the nose clamp to be arranged on the nose such that a pressure is applied to the nostrils only.

As illustrated in FIGS. 12 and 13, the protrusions 24 may further comprise a plurality of mini-protrusions 25 or mini-indentations 25. "Mini" refers to dimension in the order of millimetres.

As illustrated in FIGS. 12 and 13, the mid-section 19 of the nose clamp may comprise a plurality of traverse indentations 26. The plurality of traverse indentations 26 allows the coating to be easily bended.

FIG. 14A shows a three-dimensional view of the aluminium strip 21 to be located within the nose clamp illustrated in FIG. 13B. FIG. 14B illustrates the nose clamp of FIG. 13B with only half a coating and thus the arrangement of the aluminium strip 21 within the coating 22 is visible. FIG. 14C shows a cross-sectional view of the nose clamp of FIG. 12B, such that the arrangement of the aluminium strip 21 within the coating 22 can be viewed.

The nose clamp 17 of the present invention is configured to be arranged on the mouth piece 2 of the breathing device 1 of the present invention, when the nose clamp is not in use. When in use, the nose clamp 17 is detached from the mouth piece 2 and used as described above.

The materials of the coating and the strip 21 (which may be other materials than aluminium) are selected so that it applies a firm clamp on the nostrils of sufficient strength to collapse the nostrils while at the same time not causing discomfort to the user.

Figure 17:
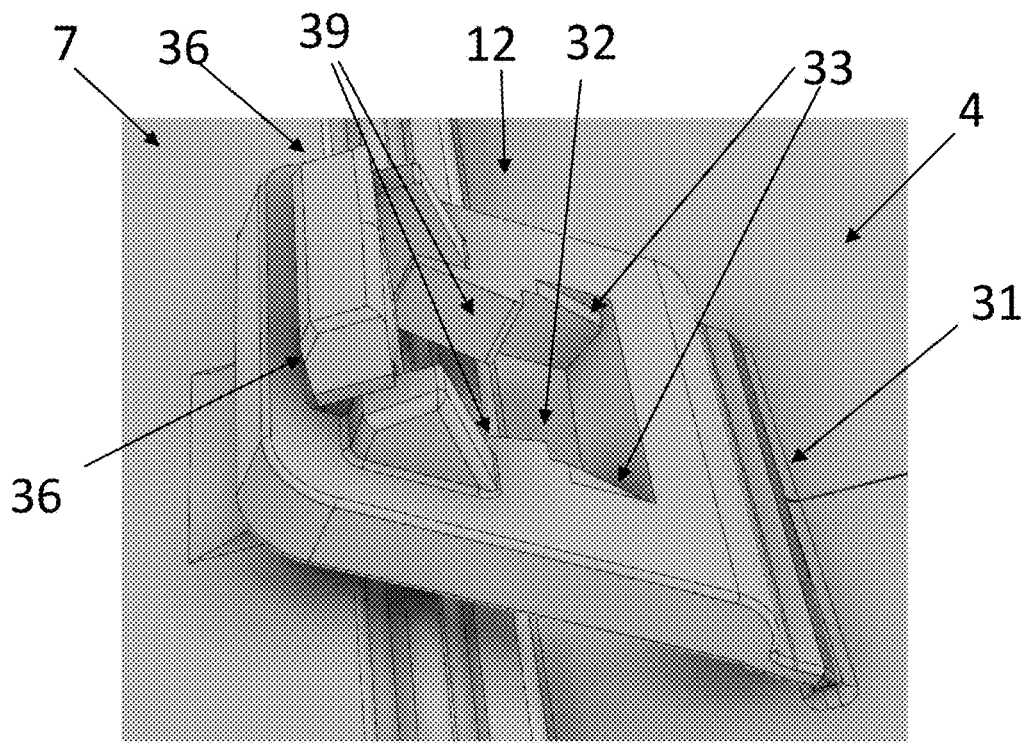
FIGS. 17 and 18 both illustrate in close-ups a latch arranged to interlock the wall member and the mouth piece.
Figure 18:
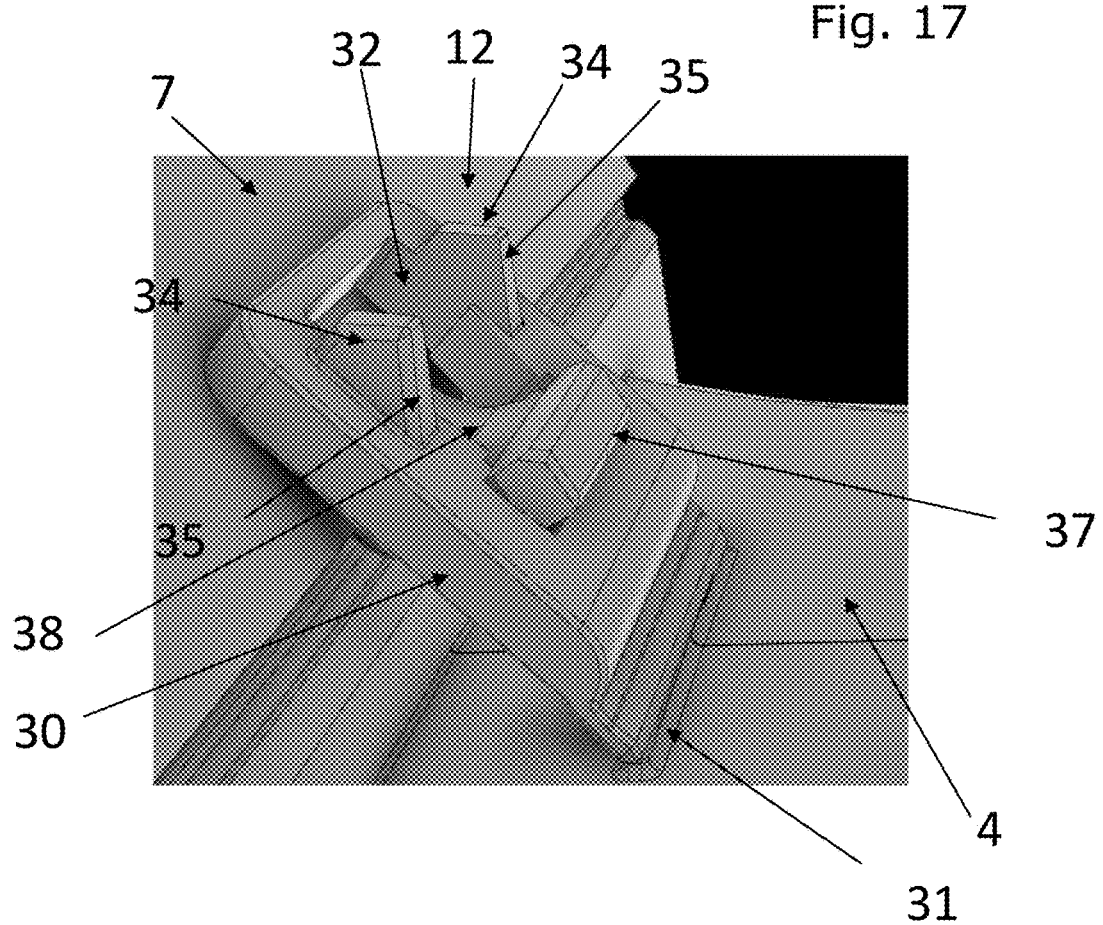

Reference is made to FIGS. 17 and 18 both illustrating in a close-up a latch 12 arranged to interlock the wall member 7 and the mouth piece 2 as disclosed e.g. in connection with FIG. 3. In FIG. 17, the wall member 7 is angled 25 degrees (see FIG. 7 for the definition of the angle) and in FIG. 18, the wall member is angled 90 degrees (which resembles the position shown in FIG. 9).

As illustrated, the latch 12 comprises a hinged and generally flat member 30 connected rotatably to the mouth piece 2 by the hinge 31, which is provided by a local thinning and a flexibility of the material from which the flat member 30 is made. The flat member 30 comprises an opening 32 through which a protruding member 37, rigidly arranged on the wall member 7, extends.

The protruding member 33 has an anvil-like shape with the arms 36 of the anvil extending above an upper surface of the flat member 30 as illustrated.

The opening 32 is irregularly shaped and comprises two landings 33 in the form of ledges inclined downwardly relative to the surface of the flat member 30 and a tapering section 39 narrowing towards the landings 33. The flat member 30 further comprises two uprights 34 each having a slanted leading edge 35.

Thus, and as illustrated, the tapering section is arranged between the two landings 33 and the two uprights 34. The two uprights, the tapering section 39 and the two landings 33 are symmetrically arranged along a centre line of the flat member 30.

In a preferred mode of use, the breathing device is provided to the user in the configuration shown in 11, and with reference to FIG. 17 the latch 12 is in such a configuration as shown. As can be seen from FIG. 17, the two arms 36 of the protruding member 37 each rests on an upper surface of the uprights 34 and since these upper surfaces are slanted downwardly toward the flat member 30, the protruding member is maintained in the position shown until a force of sufficient size is applied to the mouth piece 2 and wall member 11 to push the rod 38 towards the tapering section 39 which enlarges the opening and allows the arms 36 to pass in-between the two uprights 34 and lands in the two landings 33 which provides a locking. Thus, as disclosed the latch has a locking action according to which the wall member 7 may be positioned in two locked positions (25 and 90 degrees) by the protruding member 37 being fixed in one of the positions shown in FIGS. 17 and 18 respectively.

Figure 19:
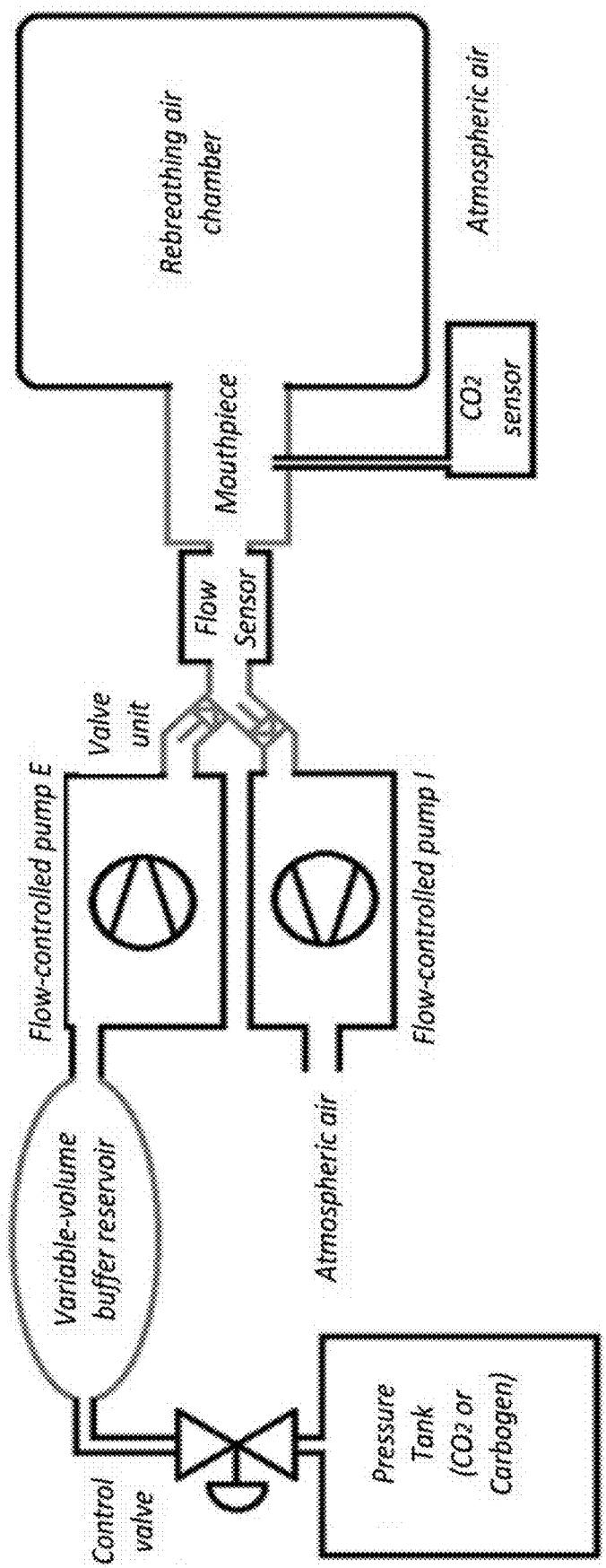
FIG. 19 schematically illustrates a test setup for testing RBR for preferred embodiments of the rebreathing device according to the invention.

Suggested Test of RBR for Embodiments of Rebreathing Device According to the Invention Reference is made to FIG. 19 schematically illustrating an experimental setup comprising:

1) A pressure tank containing carbogen (5% CO2, 15% O2, 80% N2)
2) A control valve regulating the flow of carbogen into:
3) A variable-volume buffer reservoir, the function of which is to deliver carbogen to the expiration pump E at constant atmospheric pressure
4) Expiration pump E, producing a variable flow into the rotary valve unit
5) Inspiration pump I, producing a variable flow out of the rotary valve unit
6) A flow sensor measuring the flow into and out of the mouthpiece. For these measurements an SFM3000-200C bi-directional thermistor-based flow sensor (Sensirion, Switzerland) can be used. This sensor has the form of a short pipe (23 mm in diameter, 82 mm in length) which constitutes the flow connection between the mouthpiece and the valve unit
7) The mouthpiece of the rebreathing device being tested. A sampling line is fixed in the centre of the air flow through the mouthpiece, a small pump continually drawing gas into and through:
8) A CO2 sensor (such as SpintIR6S, Gas Sensing Solutions, Scotland) measuring CO2 gas fraction (FCO2) with a high (=higher than 10 Hz) sampling rate.
9) The rebreathing air chamber of the rebreathing device.
10) A rotary valve unit connecting the pumps to the mouthpiece of the rebreathing device. The unit is controlled so as to open and close in a cyclic rhythm (the number of cycles per minute being controllable by a variable-voltage electrical motor). The number of cycles per minute should be 10, simulating a normal breathing rhythm. Such a valve unit is shown in an exploded view in FIG. 20.

Figure 20:
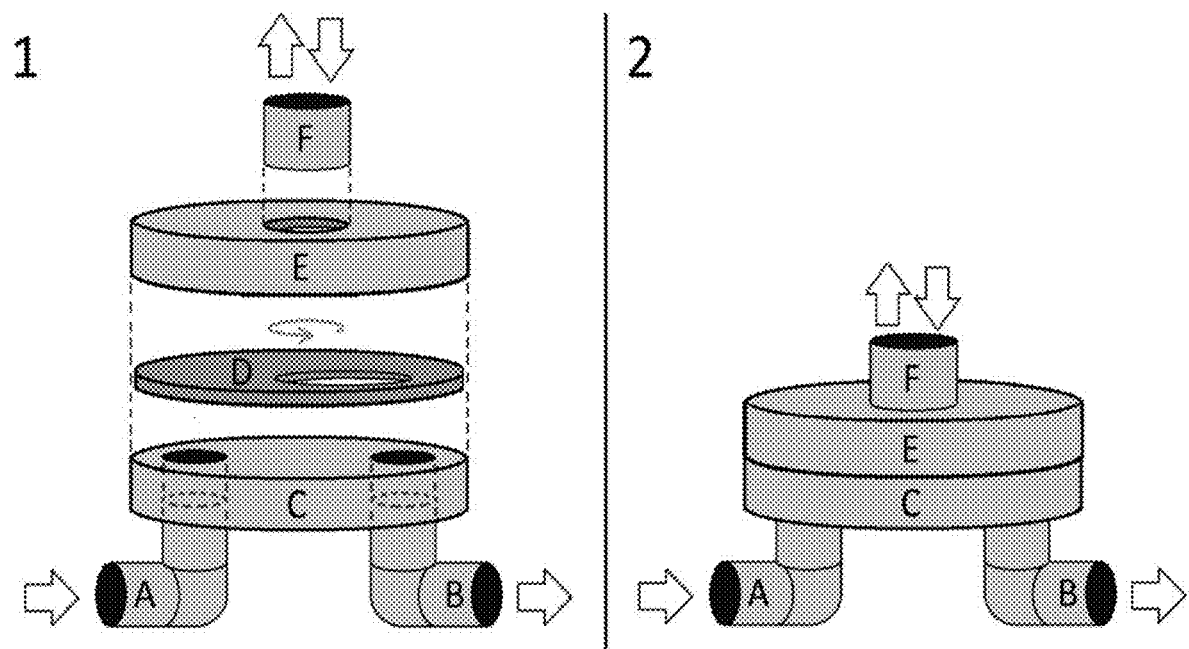
FIG. 20 illustrates exploded (1) and unexploded (2) views of the rotary valve used in the test setup of FIG. 19.

FIG. 20 illustrates exploded (1) and unexploded (2) views of the rotary valve unit with the following used legends: A: Expiration pipe, carrying carbogen gas from the carbogen reservoir to the rotary valve unit, B: Inspiration pipe, carrying mixed gas from the rotary valve unit to the surrounding atmosphere, C: Static bottom of the valve unit, through-cut by the expiration and inspiration pipes, D: Rotating disc with a single oblong aperture, alternately exposing the aperture of the expiration or inspiration pipe, E: Static top of the valve unit, through-cut by the pipe F connecting the valve unit to the mouthpiece of the rebreathing device.

A useable test procedure comprises the following steps:
1) The carbogen reservoir and the rebreathing air chamber are collapsed in order to ensure that they contain no atmospheric air.

2) The rotating disc (D in FIG. 20) is rotated to a position in which it blocks the flow of carbogen from the carbogen reservoir to the mouthpiece of the rebreathing device, specifically it is rotated to the position in which the hole in the rotating disc has rotated past the upwards-facing opening of inspiration pipe B but has not yet started to expose the upwards-facing opening of the expiration pipe A.
3) The control valve on the pressure tank is opened, allowing carbogen to flow into the variable-volume carbogen buffer reservoir.
4) The rotary valve unit rotation is turned on, starting at expiration, at which point carbogen flows through the rotary valve unit and into the rebreathing air chamber, expanding the rebreathing air chamber.
5) By rotating further, the rotary valve unit changes to the inspiration phase, drawing out of the rebreathing air chamber a mixture of A) carbogen and B) atmospheric air entering the rebreathing air chamber through the through-going openings 11 in the wall member 7.

The process 1-5 is repeated for a minimum of 60 seconds, corresponding to at least nine rotary valve unit breathing cycles.

Figure 21:
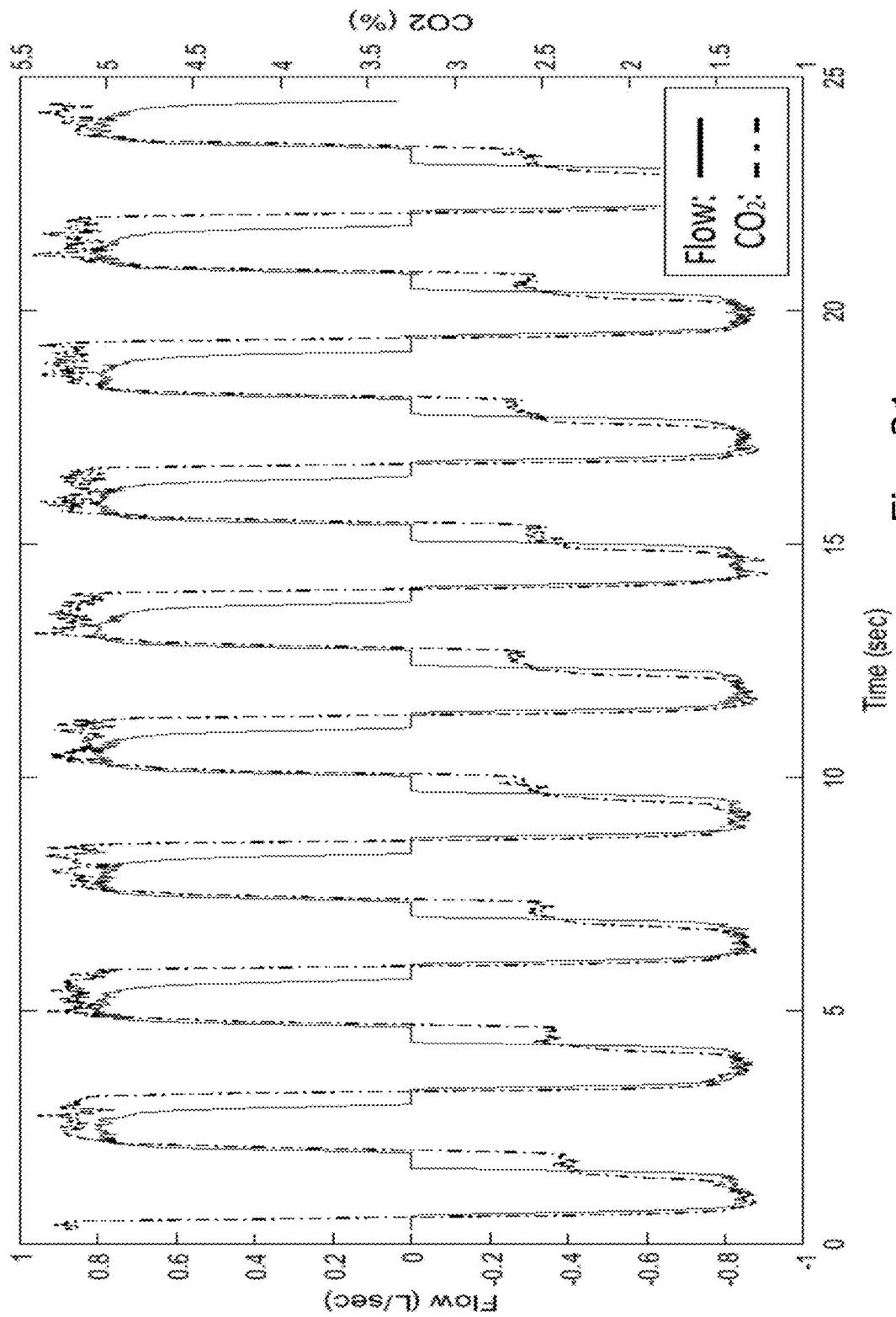
FIG. 21 is a graph illustrating the result of $CO_2$ and flow being continuously measured, producing graphs over time.

CO2 and flow is continuously measured, producing graphs over time such as shown in FIG. 21.

The RBR with a given breathing device at a given fresh air valve setting (FAVS) can based on the sensor measurements be calculated as:

$$RBR = \frac{\text{inspired volume of gas originating in the gas bottle}}{\text{total inspired volume}} =$$

$$\frac{(\text{inspired CO}_2 \text{ volume})/(\text{CO}_2 \text{ fraction in bottle gas})}{\text{total inspired volume}} =$$

$$\frac{\sum_{t=SI}^{EI} \left(F_{CO2}(t) \times \dot{V}(t) \times \Delta t\right)}{F_{CO2,bottle} \times \sum_{t=SI}^{EI} \left(\dot{V}(t) \times \Delta t\right)},$$

where t=time, SI and EI=the time points at which inspiration started and ended respectively (can be identified from the flow curve), $F_{CO2}(t)$=the $CO_2$ fraction sensor reading at time t, $\dot{V}'(t)$=the flow sensor reading at time t, $\Delta t$=the time interval between two consecutive sensor readings, $F_{CO2,bottle}$=$CO_2$ fraction of the bottle feed gas.

Although the present invention has been described in connection with the specified embodiments, it should not be construed as being in any way limited to the presented examples. The scope of the present invention is to be interpreted in the light of the accompanying claim set. In the context of the claims, the terms "comprising" or "comprises" do not exclude other possible elements or steps. Also, the mentioning of references such as "a" or "an" etc. should not be construed as excluding a plurality. The use of reference signs in the claims with respect to elements indicated in the figures shall also not be construed as limiting the scope of the invention. Furthermore, individual features mentioned in different claims may possibly be advantageously combined, and the mentioning of these features in different claims does not exclude that a combination of features is not possible and advantageous.

LIST OF REFERENCES

1: Breathing device
2: Mouthpiece
3: First end
4: Second end
5: Breathing opening
6: Rebreathing air chamber
7: Wall member
8: Through-going openings
9: Slider
10: Wall section
11: Longitudinal vent holes
12: Latch
13: Obliquely shaped through-going openings
14: Sensor for measuring oxygen level in blood
15: Portable electronic device, such as a smartphone
16: Packaging containing a breathing device
17 Nose clamp
18 First end section
19 Mid-section
20 Second end section
21 Aluminium strip
22 Coating
23 Space between first end section and second end section in curved configuration
24 Protrusion on first end section and/or second end section
25 Mini-protrusions or mini-indentations
26 Transverse indentations
27 Vice
28 Force—the arrows show the direction of applied forces during testing of a nose clamp's elastic limit
29 Digital weight scale
41: Ridge
42: Projection

The invention claimed is:

1. A system for adjusting the rebreathing ratio (RBR) of a user, the system comprising:
   a breathing device comprising:
      a mouthpiece forming a breathing channel to form a connection between a first end and a second end of the mouthpiece, the first end being configured to accommodate a user breathing into the mouthpiece through a breathing opening;
      an at least partly flexible rebreathing air chamber arranged in fluid communication with the second end of the mouthpiece, thereby being in fluid connection with the breathing channel through the second end of the mouthpiece, the rebreathing air chamber being formed by at least partly flexible wall section(s);
      a wall member pivotally connected to the second end of the mouthpiece and forming part of the rebreathing air chamber, said wall member comprising one or more through-going openings provided in the wall member at the second end of the mouthpiece, allowing fluid communication between the rebreathing air chamber and the surrounding atmosphere, said one or more through-going openings being re-closeable or adjustable in size, and
      a computer configured to automatically determine whether to change the RBR based on the user's response to a questionnaire in data connection with said computer,
   wherein the system is configured to signal the user to change a setting of the re-closeable or adjustable one or more through-going openings, if when the RBR is determined to be changed by the computer based on the data from the questionnaire.

2. The system according to claim 1, wherein said one or more through-going openings have a first conductance $G_{out}$ and said rebreathing air chamber being impermeable to gas has a second conductance $G_{expand}$, and wherein the one or more through-going openings and the rebreathing air chamber are configured to provide a RBR defined as RBR $G_{expand}/(G_{out}+G_{expand})$ between 0.5 and 0.95, or between 0.2 and 0.65.

3. The system according to claim 1, wherein the system comprises a nose clamp comprising a bendable elongated strip and a coating surrounding the strip on all sides.

4. A method for adjusting the rebreathing ratio (RBR) of a breathing device with an adjustable RBR and a computer configured to automatically determine whether to change the RBR based on a user's response to a questionnaire, the method comprising:
   providing a breathing device comprising:
      a mouthpiece forming a breathing channel to form a connection between a first end and a second end of the mouthpiece, the first end being configured for a user breathing into the mouthpiece through a breathing opening;
      an at least partly flexible rebreathing air chamber arranged in fluid communication with the second end of the mouthpiece, thereby being in fluid connection with the breathing channel through the second end of the mouthpiece, the rebreathing air chamber being formed by at least partly flexible wall section(s);
      a wall member pivotally connected to the second end of the mouthpiece and forming part of the rebreathing air chamber;
      one or more through-going openings provided in the wall member at the second end of the mouthpiece, allowing fluid communication between the rebreathing air chamber and the surrounding atmosphere, said one or more through-going openings being re-closeable or adjustable in size;
   the user breathing through the breathing device;
      executing a questionnaire containing questions relating to the user's response to the use of the breathing device during use of the breathing device,
      in response thereto determining by use of the computer whether to change the RBR, and
      when the RBR is determined to be changed, signalling to the user a new setting for the breathing device.

5. The method according to claim 4, wherein the RBR is changed via a setting of a slider position, each setting corresponding to a specific position of member at the second end of the mouthpiece to cover a portion of the one or more through-going openings.

6. The method for adjusting the RBR according to claim 4, wherein a kit of parts is utilized and said kits of parts comprises:
   the breathing device; and
      a $SpO_2$-sensor measuring an arterial oxygenation value of the user and a $CO_2$ sensor fluidly connected to the breathing device, the $SpO_2$ sensor and the $CO_2$ sensor being in data connection with the computer.

7. The method for adjusting the RBR according to claim 4, wherein the computer is a smartphone.

8. The method for adjusting the RBR according to claim 4, wherein the computer is a tablet or a smartphone.

9. The method for adjusting the RBR according to claim 4, wherein the computer has a number of pre-stored baseline settings, each setting corresponding to a slider position or a number of said one or more through-going openings being closed.

10. The method for adjusting the RBR according to claim 4, wherein the computer has a number of pre-stored baseline settings, each setting corresponding to a geographical position.

11. The method for adjusting the RBR according to claim 4, wherein the computer has a number of pre-stored baseline settings, each setting corresponding to previous changes in the RBR or user data including gender, age and type of disease.

* * * * *